US 6,611,715 B1

(12) United States Patent
Boveja

(10) Patent No.: US 6,611,715 B1
(45) Date of Patent: *Aug. 26, 2003

(54) APPARATUS AND METHOD FOR NEUROMODULATION THERAPY FOR OBESITY AND COMPULSIVE EATING DISORDERS USING AN IMPLANTABLE LEAD-RECEIVER AND AN EXTERNAL STIMULATOR

(76) Inventor: Birinder R. Boveja, P.O. Box 210095, Milwaukee, WI (US) 53221

( * ) Notice: Subject to any disclaimer, the term of this patent is extended or adjusted under 35 U.S.C. 154(b) by 110 days.

This patent is subject to a terminal disclaimer.

(21) Appl. No.: 09/837,661

(22) Filed: Apr. 19, 2001

Related U.S. Application Data

(63) Continuation-in-part of application No. 09/727,570, filed on Nov. 30, 2000, now Pat. No. 6,356,788, which is a continuation-in-part of application No. 09/178,060, filed on Oct. 26, 1998, now Pat. No. 6,205,359.

(51) Int. Cl.[7] .................................................. A61N 1/36
(52) U.S. Cl. ....................................................... 607/40
(58) Field of Search ........................... 607/1–2, 40, 33, 607/59–62, 65–66, 133, 118; 128/897–899

(56) References Cited

U.S. PATENT DOCUMENTS

| 3,760,812 | A |   | 9/1973  | Timm et al. ................ 128/418 |
| 3,796,221 | A |   | 3/1974  | Hagfors et al. ............. 128/421 |
| 4,573,481 | A | * | 3/1986  | Bullara ....................... 607/118 |
| 4,702,254 | A |   | 10/1987 | Zabara et al. ............... 128/421 |
| 4,867,164 | A |   | 9/1989  | Zabara et al. ............... 128/421 |
| 4,979,511 | A |   | 12/1990 | Terry et al. ................. 128/642 |
| 5,025,807 | A |   | 6/1991  | Zabara et al. ............... 128/421 |
| 5,263,480 | A | * | 11/1993 | Wernicke et al. ........... 607/118 |
| 5,304,206 | A |   | 4/1994  | Baker et al. .................... 607/2 |
| 5,571,150 | A | * | 11/1996 | Wernicke et al. ............. 607/72 |
| 5,611,350 | A | * | 3/1997  | John ............................. 600/378 |
| 5,690,693 | A | * | 11/1997 | Wang et al. ................... 607/61 |
| 5,755,766 | A | * | 5/1998  | Chastain et al. ............ 607/119 |
| 6,205,359 | B1 | * | 3/2001  | Boveja ......................... 607/45 |

OTHER PUBLICATIONS

J. S. Davidson et al Mechanical properties and sensitivity to CCK . . . Am. J. Physiology (1988) 255, G55–G61.

* cited by examiner

Primary Examiner—Kennedy Schaetzle
Assistant Examiner—Kristen Droesch

(57) ABSTRACT

A system and method of neuromodulation adjunct (add-on) therapy for obesity and compulsive eating disorders, comprises an implantable lead-receiver and an external stimulator. Neuromodulation is performed using pulsed electrical stimulation. The external stimulator contains a power source, controlling circuitry, a primary coil, and predetermined programs which control the different levels of therapy. The primary coil of the external stimulator inductively transfers electrical signals to the lead-receiver, which is also in electrical contact with the left vagus nerve. The external stimulator emits electrical pulses to stimulate the vagus nerve according to a predetermined program. In a second mode of operation, an operator may manually override the predetermined sequence of stimulation. The predetermined programs have different levels of control, which is password protected. The external stimulator may also be equipped with a telecommunications module to control the predetermined programs remotely.

63 Claims, 31 Drawing Sheets (PRIOR ART - US Patent 5,263,480)

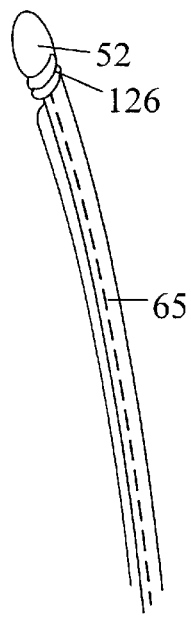
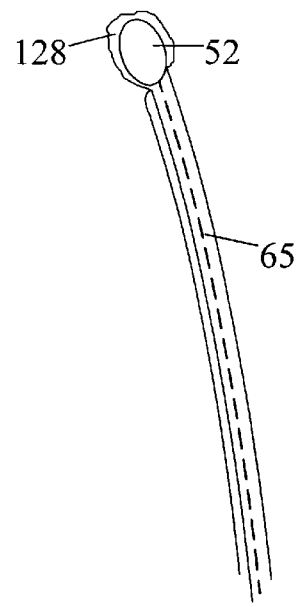
FIG. 32    FIG. 33
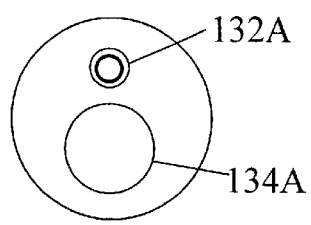 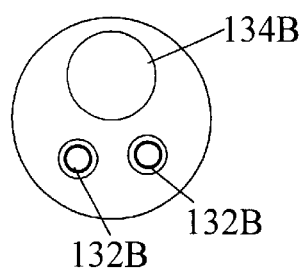 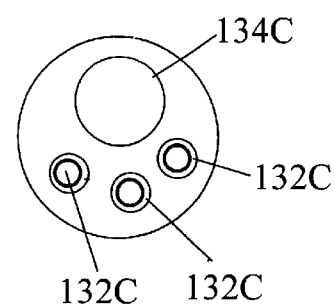
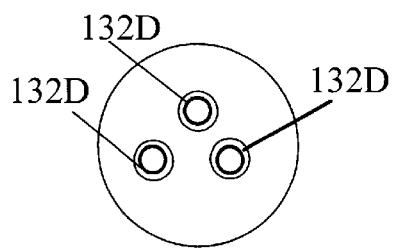 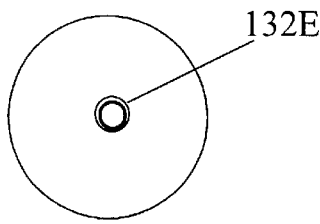 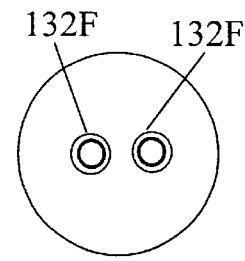
FIG. 34

APPARATUS AND METHOD FOR NEUROMODULATION THERAPY FOR OBESITY AND COMPULSIVE EATING DISORDERS USING AN IMPLANTABLE LEAD-RECEIVER AND AN EXTERNAL STIMULATOR

This is a Continuation-in-Part application of Ser. No. 09/727,570 filed Nov. 30, 2000, now U.S. Pat. No. 6,356,788 which is a Continuation-in-Part of Ser. No. 09/178,060 filed Oct. 26, 1998, now U.S. Pat. No. 6,205,359. Priority is claimed from these applications, and the prior applications being incorporated herein by reference. Further, this application is related to the following applications filed Apr. 17, 2001, entitled, a) Apparatus and method for electrical stimulation adjunct (add-on) therapy of atrial fibrillation, inappropriate sinus tachycardia, and refractory hypertension with an external stimulator b) Apparatus and method for adjunct (add-on) treatment of coma and traumatic brain injury with neuromodulation using an external stimulator.

c) Apparatus and method for adjunct (add-on) treatment of diabetes by neuromodulation with an external stimulator.

FIELD OF INVENTION

This invention relates generally to medical device used for adjunct (add-on) treatment for obesity, more specifically a medical device used for adjunct (add-on) therapy for obesity and compulsive eating disorders with electrical stimulation neuromodulation using an implanted lead-receiver and an external stimulator.

BACKGROUND

Obesity results from excessive accumulation of fat in the body. It is caused by ingestion of greater amounts of food than can be used by the body for energy. The excess food, whether fats, carbohydrates, or proteins, is then stored almost entirely as fat in the adipose tissue, to be used later for energy. There can be various causes of obesity including, psychogenic, neurogenic, genetic, and other metabolic related factors. Treatment of obesity depends on decreasing energy input below energy expenditure. Treatment has included among other things various drugs, starvation and even stapling or surgical resection of a portion of the stomach.

The $10^{th}$ cranial nerve or the vagus nerve plays a role in mediating afferent information from the stomach to the satiety center in the brain. The vagus nerve arises directly from the brain, but unlike the other cranial nerves extends well beyond the head. At its farthest extension it reaches the lower parts of the intestines. This is shown schematically in FIG. 1A, and in more detail in FIG. 1B.

Observations on the profound effect of electrical stimulation of the vagus nerve on central nervous system (CNS) activity extends back to the 1930's. In 1988 it was reported in the *American Journal of Physiology*, that the afferent vagal fibers from the stomach wall increased their firing rate when the stomach was filled. Accordingly, extra-physiologic electrical stimulation of the vagus nerve, from just above the stomach level, should produce appetite supression by causing the patient to experience satiety.

The present invention is primarily directed to apparatus and method for electrical stimulation neuromodulation of the vagus nerve, to treat compulsive overeating and obesity with an implanted lead-receiver and an external stimulator with predetermined programs. Upon experiencing the compulsive craving, the obese patient can voluntarily activate the stimulus generator by activating a predetermined program.

The vagus nerve 54 provides an easily accessible, peripheral route to modulate central nervous system (CNS) function. In the human body there are two vagus nerves (VN), the right VN and the left VN. Each vagus nerve is encased in the carotid sheath along with the carotid artery and jugular vein. The innervation of the right and left vagus nerves is different. The innervation of the right vagus nerve is such that stimulating it results in profound bradycardia (slowing of the heart rate). The left vagus nerve has some innervation to the heart, but mostly innervates the visceral organs such as the gastrointestinal tract. It is known that stimulation of the left vagus nerve does not cause any significant deleterious side effects.

Neuromodulation

One of the fundamental features of the nervous system is its ability to generate and conduct electrical impulses. These can take the form of action potentials, which is defined as a single electrical impulse passing down an axon, and is shown schematically in FIG. 2. The top portion of the figure (A) shows conduction over mylinated axon (fiber) and the bottom portion (B) shows conduction over nonmylinated axon (fiber). These electrical signals will travel along the nerve fibers.

The nerve impulse (or action potential) is an "all or nothing" phenomenon. That is to say, once the threshold stimulus intensity is reached an action potential 7 will be generated. This is shown schematically in FIG. 3. The bottom portion of the figure shows a train of action potentials.

Most nerves in the human body are composed of thousands of fibers of different sizes. This is shown schematically in FIG. 4. The different sizes of nerve fibers, which carry signals to and from the brain, are designated by groups A, B, and C. The vagus nerve, for example, may have approximately 100,000 fibers of the three different types, each carrying signals. Each axon or fiber of that nerve conducts only in one direction, in normal circumstances.

In a cross section of peripheral nerve it is seen that the diameter of individual fibers vary substantially. The largest nerve fibers are approximately 20 $\mu$m in diameter and are heavily myelinated (i.e., have a myelin sheath, constituting a substance largely composed of fat), whereas the smallest nerve fibers are less than 1 $\mu$m in diameter and are unmyelinated. As shown in FIG. 5, when the distal part of a nerve is electrically stimulated, a compound action potential is recorded by an electrode located more proximally. A compound action potential contains several peaks or waves of activity that represent the summated response of multiple fibers having similar conduction velocities. The waves in a compound action potential represent different types of nerve fibers that are classified into corresponding functional categories as shown in the table below,

| Fiber Type | Conduction Velocity (m/sec) | Fiber Diameter (μm) | Myelination |
|---|---|---|---|
| A Fibers | | | |
| Alpha | 70–120 | 12–20 | Yes |
| Beta | 40–70 | 5–12 | Yes |
| Gamma | 10–50 | 3–6 | Yes |
| Delta | 6–30 | 2–5 | Yes |
| B Fibers | 5–15 | <3 | Yes |
| C Fibers | 0.5–2.0 | 0.4–1.2 | No |

The diameters of group A and group B fibers include the thickness of the myelin sheaths. Group A is further subdivided into alpha, beta, gamma, and delta fibers in decreasing order of size. There is some overlapping of the diameters of the A, B, and C groups because physiological properties, especially in the form of the action potential, are taken into consideration when defining the groups. The smallest fibers (group C) are unmyelinated and have the slowest conduction rate, whereas the myelinated fibers of group B and group A exhibit rates of conduction that progressively increase with diameter.

Compared to unmyelinated fibers, myelinated fibers are typically larger, conduct faster, have very low stimulation thresholds, and exhibit a particular strength-duration curve or respond to a specific pulse width versus amplitude for stimulation. The A and B fibers can be stimulated with relatively narrow pulse widths, from 50 to 200 microseconds ($\mu s$), for example. The A fiber conducts slightly faster than the B fiber and has a slightly lower threshold. The C fibers are very small, conduct electrical signals very slowly, and have high stimulation thresholds typically requiring a wider pulse width (300–1,000 $\mu s$) and a higher amplitude for activation. Because of their very slow conduction, C fibers would not be highly responsive to rapid stimulation. Selective stimulation of only A and B fibers is readily accomplished. The requirement of a larger and wider pulse to stimulate the C fibers, however, makes selective stimulation of only C fibers, to the exclusion of the A and B fibers, virtually unachievable inasmuch as the large signal will tend to activate the A and B fibers to some extent as well.

The vagus nerve is composed of somatic and visceral afferents and efferents. Usually, nerve stimulation activates signals in both directions (bi-directionally). It is possible however, through the use of special electrodes and waveforms, to selectively stimulate a nerve in one direction only (unidirectionally). The vast majority of vagus nerve fibers are C fibers, and a majority are visceral afferents having cell bodies lying in masses or ganglia in the skull. The central projections terminate largely in the nucleus of the solitary tract, which sends fibers to various regions of the brain (e.g., the thalamus, hypothalamus and amygdala).

Vagus nerve stimulation is a means of directly affecting central function. As shown in FIG. 6, cranial nerves have both afferent pathway 19 (inward conducting nerve fibers which convey impulses toward the brain) and efferent pathway 21 (outward conducting nerve fibers which convey impulses to an effector). The vagus nerve 54 is composed of 80% afferent sensory fibers carrying information to the brain from the head, neck, thorax, and abdomen. The sensory afferent cell bodies of the vagus reside in the nodose ganglion and relay information to the nucleus tractus solitarius (NTS).

FIG. 7 shows the nerve fibers traveling through the spinothalamic tract to the brain. The afferent fibers project primarily to the nucleus of the solitary tract (shown schematically in FIG. 8) which extends throughout the length of the medulla oblongata. A small number of fibers pass directly to the spinal trigeminal nucleus and the reticular formation. As shown in FIG. 8, the nucleus of the solitary tract has widespread projection to cerebral cortex, basal forebrain, thalamus, hypothalamus, amygdala, hippocampus, dorsal raphe, and cerebellum. In summary, because of the widespread projections of the Nucleus of the Solitary Tract, neuromodulation of the vagal afferent nerve fibers produce appetite supression by causing the patient to experience satiety.

PRIOR ART

One type of medical device therapy for obesity and eating disorders is generally directed to the use of an implantable lead and an implantable pulse generator technology or "cardiac pacemaker like" technology, i.e. stimulation with an implantable Neurocybernetic Prosthesis. In the prior art, the pulse generator is programmed via a "personnel computer (PC)" based programmer that is adapted with a programmer wand, which is placed on top of the skin over the pulse generator implant site. This is shown in FIG. 9. Also, in the prior art each parameter is programmed independent of the other parameters. Therefore, millions of different combinations of programs are possible. In the current patent application, limited number of programs are pre-selected. Other relevant prior art is briefly summarized below.

U.S. Pat. No. 5,263,480 (Wernicke et al) is generally directed to treatment of eating disorders by using an implantable neurocybernetic prosthesis (NCP), which is a "cardiac pacemaker-like" device.

U.S. Pat. No. 5,304,206 (Baker, Jr. et al) is directed to activation techniques for implanted medical stimulators. The system uses either a magnet to activate the reed switch in the device, or tapping which acts through the piezoelectric sensor mounted on the case of the implanted device, or a combination of magnet use and tapping sequence.

U.S. Pat. No. 3,796,221 (Hagfors) is directed to controlling the amplitude, duration and frequency of electrical stimulation applied from an externally located transmitter to an implanted receiver by inductively coupling. Electrical circuitry is schematically illustrated for compensating for the variability in the amplitude of the electrical signal available to the receiver because of the shifting of the relative positions of the transmitter-receiver pair. By highlighting the difficulty of delivering consistent pulses, this patent points away from applications such as the current application, where consistent therapy needs to be continuously sustained over a prolonged period of time. The methodology disclosed is focused on circuitry within the receiver, which would not be sufficient when the transmitting coil and receiving coil assume significantly different orientation, which is likely in the current application. The present invention discloses a novel approach for this problem.

U.S. Pat. Nos. 4,702,254, 4,867,164 and 5,025,807 (Zabara) generally disclose animal research and experimentation related to epilepsy and the like and are directed to stimulating the vagas nerve by using "pacemaker-like" technology, such as an implantable pulse generator. The pacemaker technology concept consists of a stimulating lead connected to a pulse generator (containing the circuity and DC power source) implanted subcutaneously or submuscularly, somewhere in the pectoral or axillary region, and programming with an external personal computer (PC) based programmer. Once the pulse generator is programmed for the patient, the fully functional circuitry and power source are fully implanted within the patient's body. In such a system, when the battery is depleted, a surgical procedure is required to disconnect and replace the entire pulse generator (circuitry and power source). These patents neither anticipate practical problems of an inductively coupled system, nor suggest solutions to the same for an inductively coupled system for neuromodulation therapy.

U.S. Pat. No. 4,573,481 (Bullara) is directed to an implantable helical electrode assembly configured to fit around a nerve. The individual flexible ribbon electrodes are each partially embedded in a portion of the peripheral surface of a helically formed dielectric support matrix.

U.S. Pat. No. 3,760,812 (Timm et al.) discloses nerve stimulation electrodes that include a pair of parallel spaced apart helically wound conductors maintained in this configuration.

U.S. Pat. No. 4,979,511 (Terry) discloses a flexible, helical electrode structure with an improved connector for attaching the lead wires to the nerve bundle to minimize damage.

Apparatus and method for neuromodulation, in the current application has several advantages over the prior art implantable pulse generator. The external stimulator described here can be manufactured at a fraction of the cost of an implantable pulse generator. The therapy can be freely applied with consideration of battery depletion. Surgical replacement of pulse generator is avoided. The programming is much simpler, and can be adjusted by the patient within certain limits for patient comfort. And, the implanted hardware is significantly smaller.

SUMMARY OF THE INVENTION

The system and method of the current invention also overcomes many of the disadvantages of the prior art by simplifying the implant and taking the programmability into the external stimulator. Further, the programmability of the external stimulator can be controlled remotely, via the wireless medium, as described in a co-pending application. The system and method of this invention uses the patient as his/her own feedback loop. Once the therapy is prescribed by the physician, the patient can receive the therapy as needed based on symptoms, and the patient can adjust the stimulation within prescribed limits for his/her own comfort.

The present invention is directed to system and methods for adjunct (add-on) electrical neuromodulation therapy for obesity and compulsive eating disorders, using predetermined programs with an external stimulator. The system consists of an implantable lead-receiver containing passive circuitry, electrodes, and a coil for coupling to the external stimulator. The external stimulator, which may be worn on a belt or carried in a pocket contains, electronic circuitry, power source, primary coil, and predetermined programs. The external primary coil and subcutaneous secondary coil are inductively coupled. The patient may selectively activate stimulation corresponding to meals, or leave the stimulation on according to pre-packaged program.

In one aspect of the invention the pulse generator contains a limited number of predetermined programs packaged into the stimulator, which can be accessed directly without a programmer. The limited number of programs can be any number of programs even as many as 100 programs, and such a number is considered within the scope of this invention.

In another feature of the invention, the system provides for proximity sensing means between the primary (external) and secondary (implanted) coils. Utilizing current technology, the physical size of the implantable lead-receiver has become relatively small. However, it is essential that the primary (external) and secondary (implanted) coils be positioned appropriately with respect to each other. The sensor technology incorporated in the present invention aids in the optimal placement of the external coil relative to a previously implanted subcutaneous coil. This is accomplished through a combination of external and implantable components.

In another feature of the invention, the external stimulator has predetermined programs, as well as a manual "on" and "off" button. Each of these programs has a unique combination of pulse amplitude, pulse width, frequency of stimulation, "on" time and "off" time. After the therapy has been initiated by the physician, the patient has a certain amount of flexibility in adjusting the intensity of the therapy (level of stimulation). The patient has the flexibility to decrease (or increase) the level of stimulation (within limits). The manual "on" button gives the patient flexibility to immediately start the stimulating pattern at any time. Of the pre-determined programs, patients do not have access to at least one of the programs, which can be activated only by the physician, or an appropriate person.

Various other features, objects and advantages of the invention will be made apparent from the following description taken together with the drawings.

BRIEF DESCRIPTION OF THE DRAWINGS

For the purpose of illustrating the invention, there are shown in accompanying drawing forms which are presently preferred, it being understood that the invention is not intended to be limited to the precise arrangement and instrumentalities shown.

FIG. 32 is a diagram of an electrode containing steroid drug in a silicone collar at the base of electrode.

FIG. 33 is a diagram of an electrode with steroid drug coated on the surface of the electrode.

FIG. 34 is a diagram of cross sections of implantable lead-receiver body showing different lumens.

DETAILED DESCRIPTION OF THE INVENTION

The following description is of the current embodiment for carrying out the invention. This description is not to be taken in a limiting sense, but is made merely for the purpose of describing the general principles of the invention. The scope of the invention should be determined with reference to the claims.

The system and method of neuromodulation therapy of this invention consists of delivering pulsed electrical stimulation, using an implanted lead-receiver and an external stimulator with predetermined programs of stimulation. The implanted lead-receiver and external stimulator are inductively coupled. The predetermined programs contain unique combination of stimulation parameters for neuromodulation, and differ in the aggressiveness of the therapy. Some of the predetermined programs are "locked-out" to the patient, and can be accessed and controlled by the physician only.

Figure 1A:
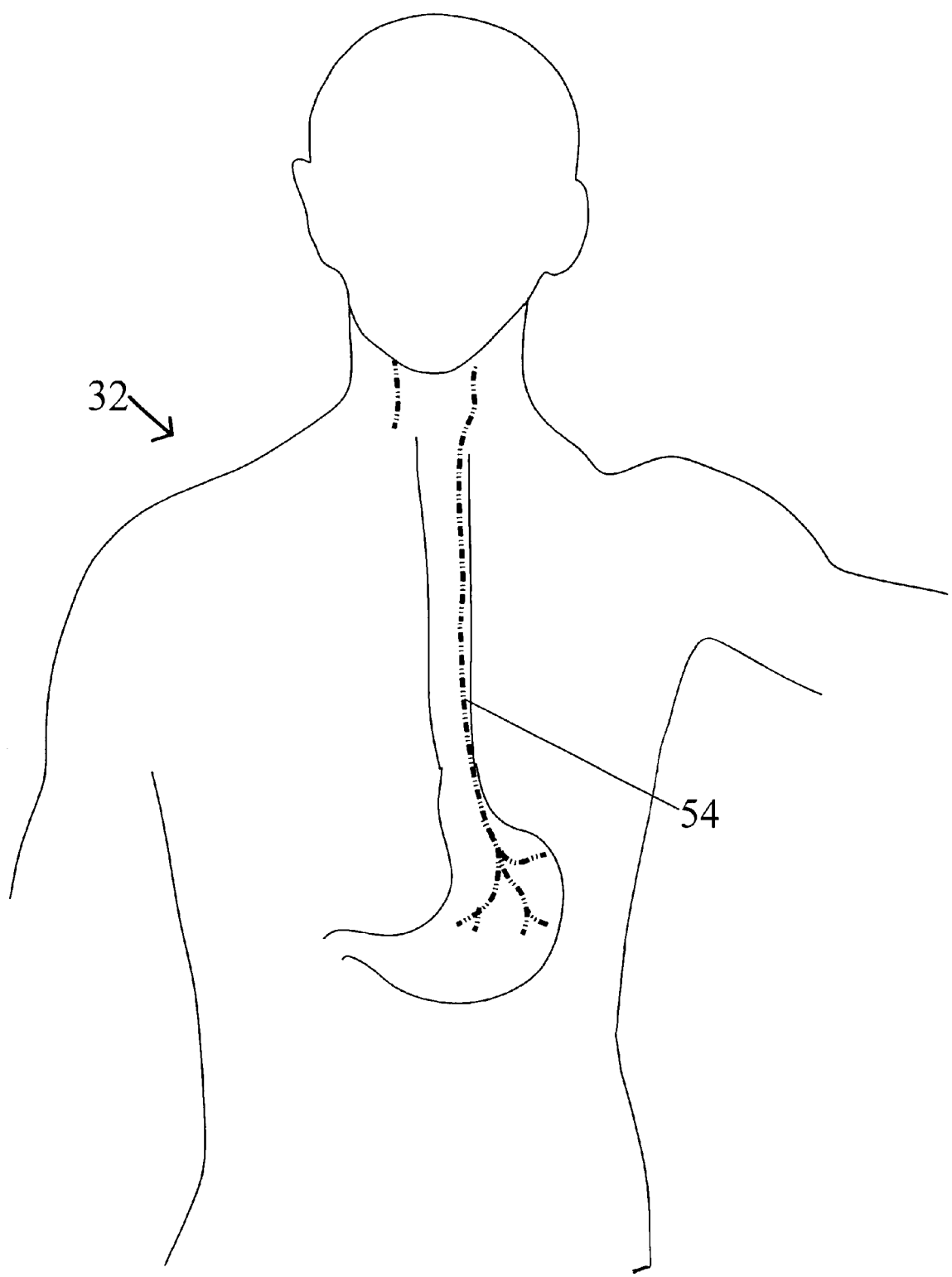
FIG. 1A is a schematic showing part of the innervation of the left vagus nerve.
Figure 1B:
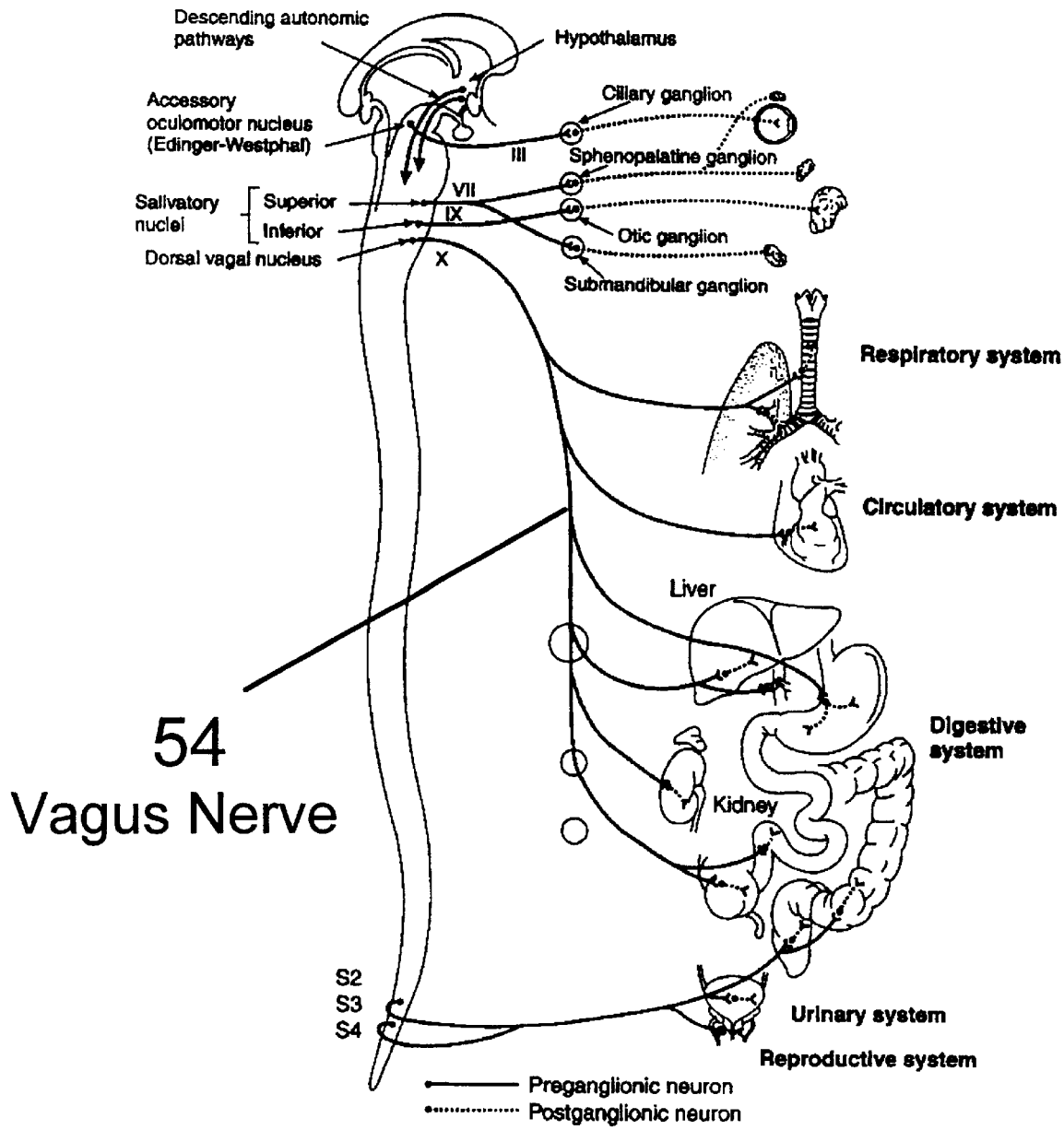
FIG. 1B is a schematic showing detailed innervation of the left vagus nerve.
Figure 2:
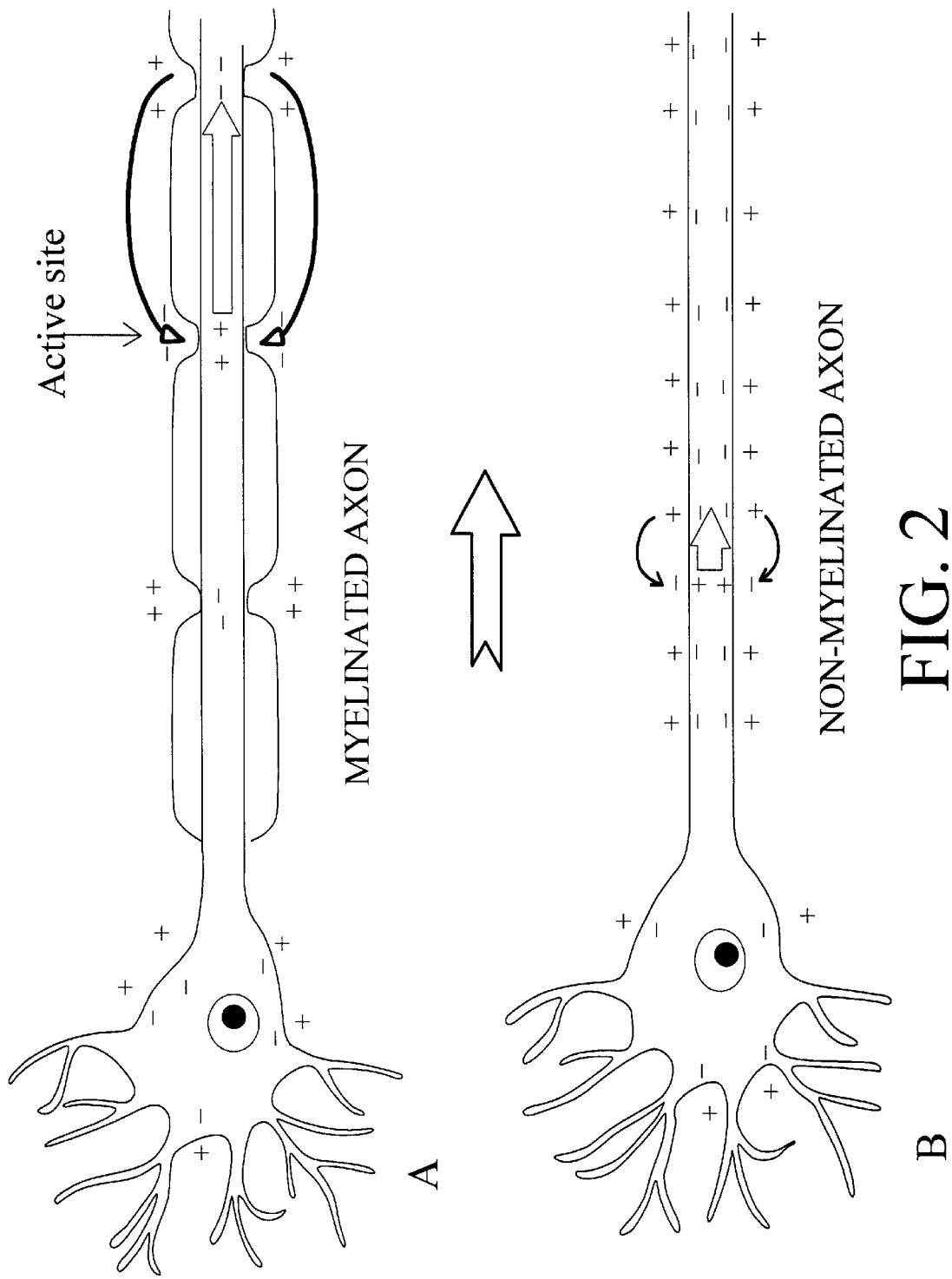
FIG. 2 is a schematic diagram of myelinated and nonmyelinated axon.
Figure 3:
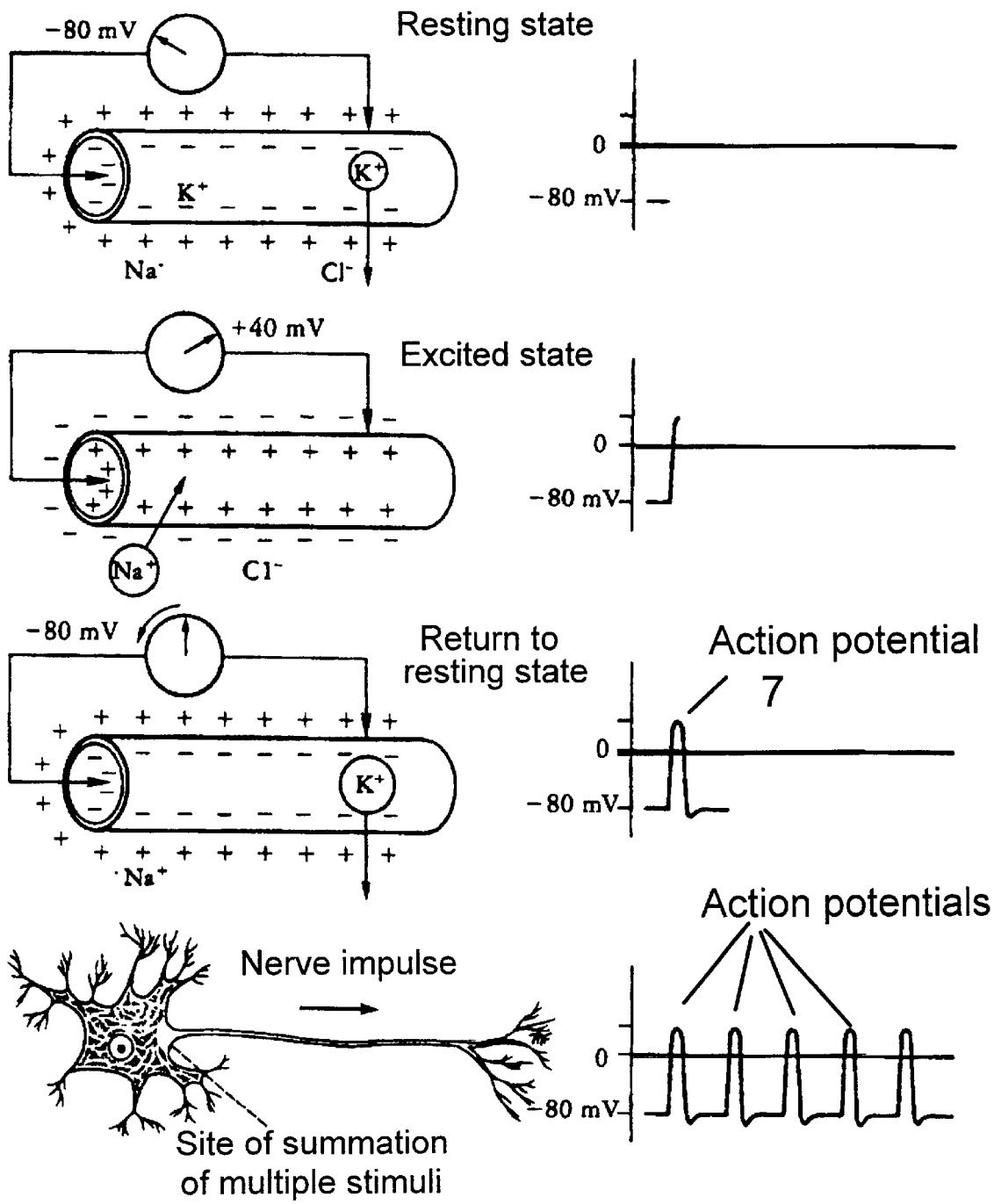
FIG. 3 is a schematic diagram of a single nerve impulse and a train of nerve impulses.
Figure 4:
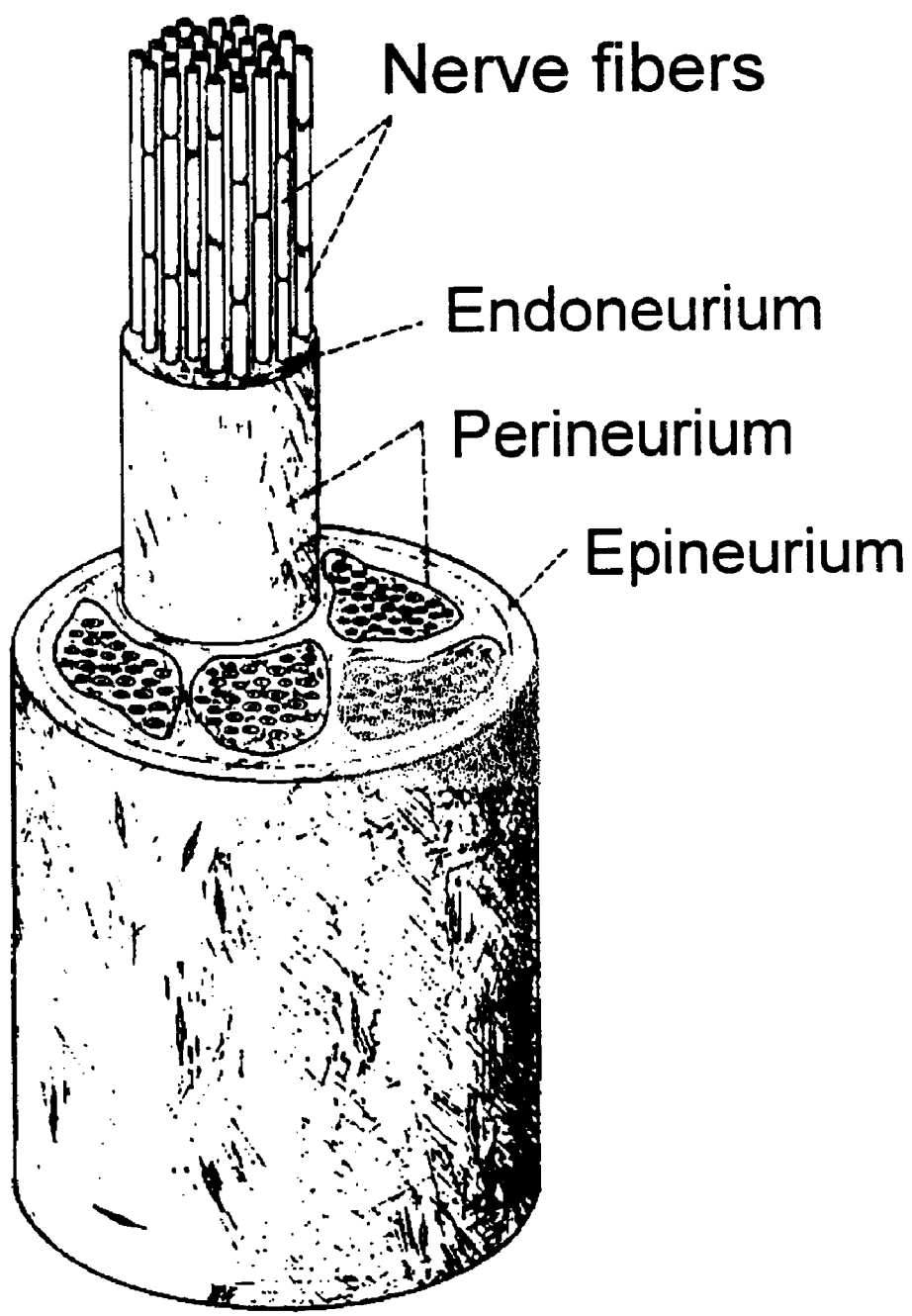
FIG. 4 is a diagram of the structure of a peripheral nerve.
Figure 5:
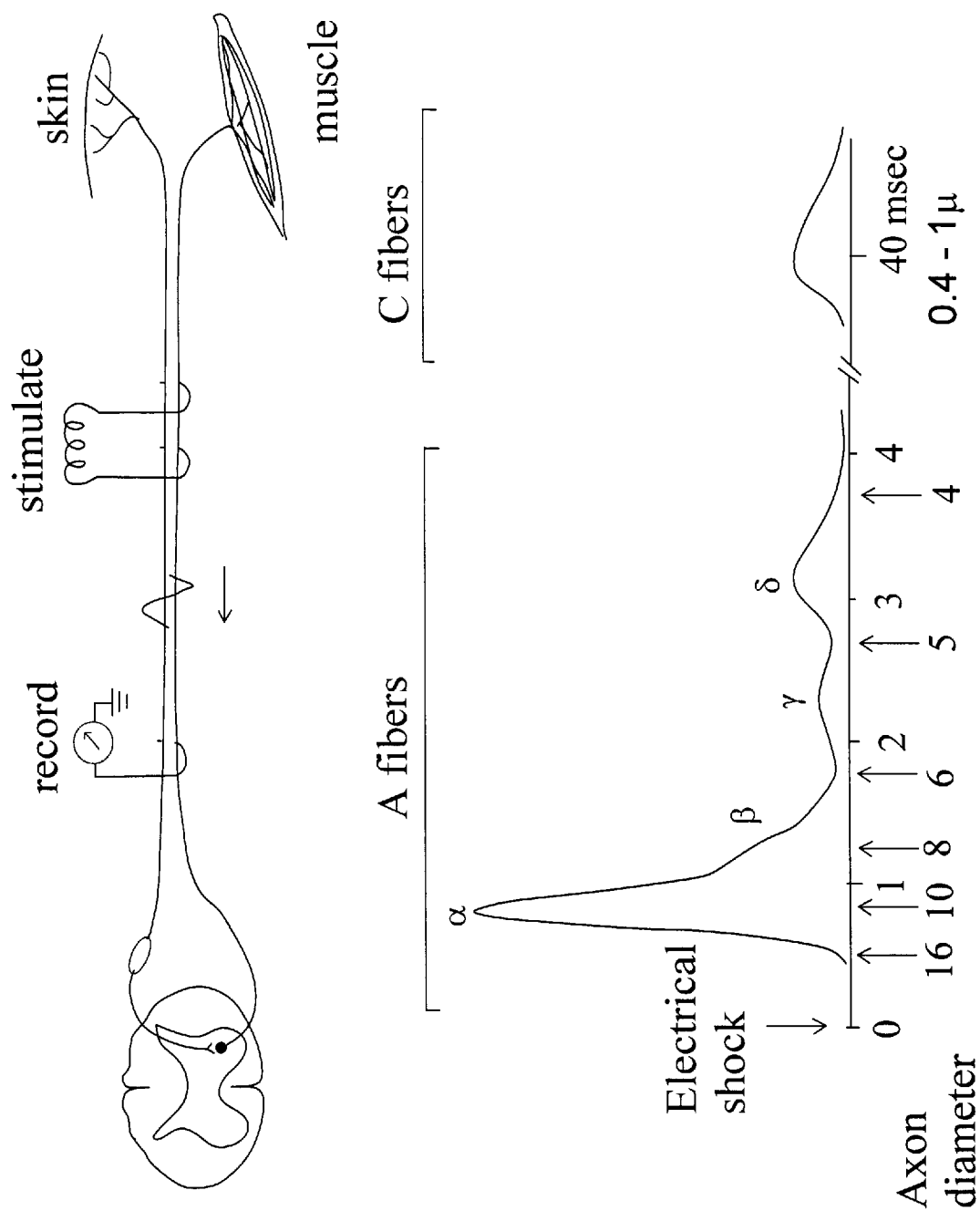
FIG. 5 is a diagram showing recordings of compound action potentials.
Figure 6:
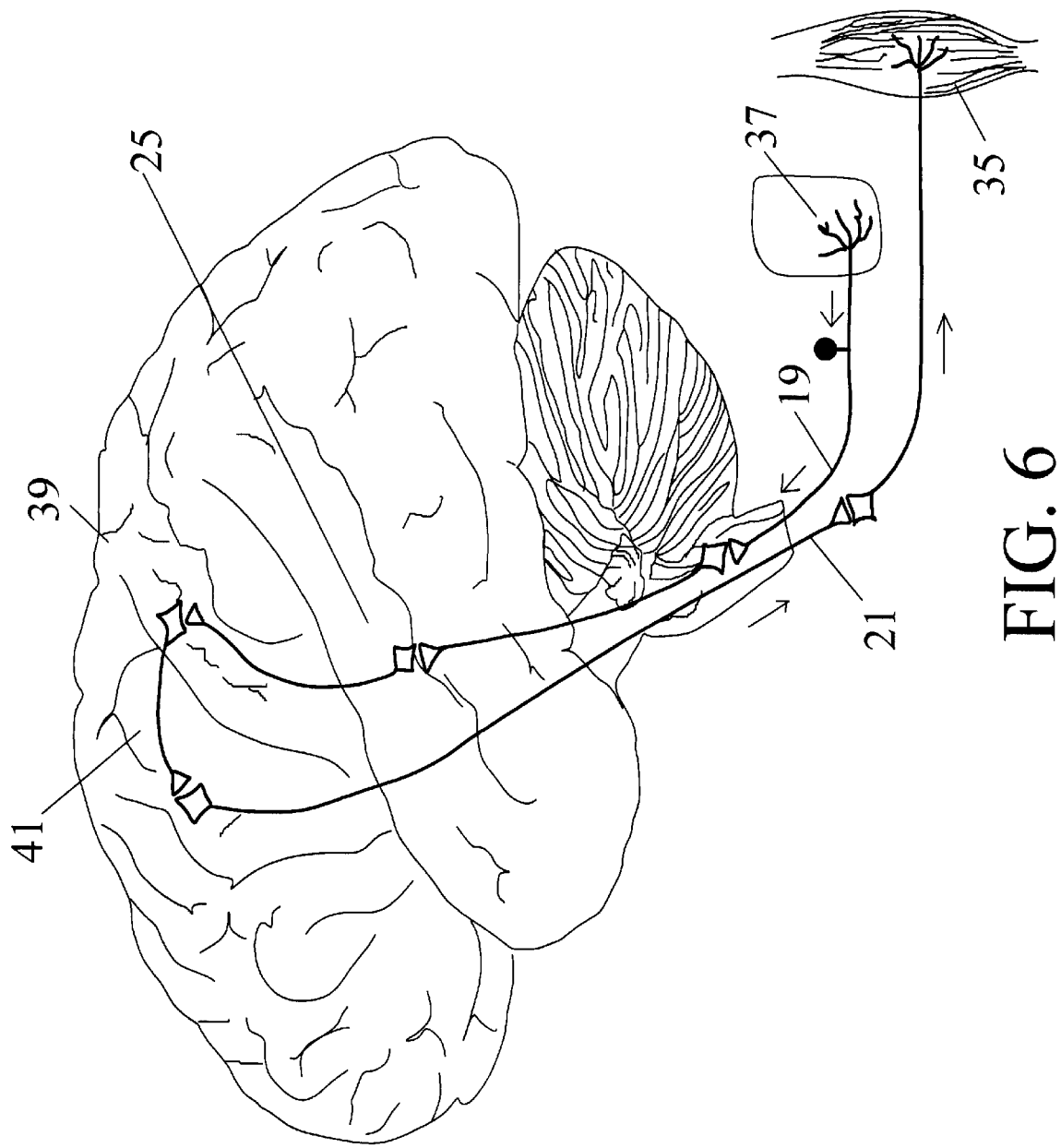
FIG. 6 is a schematic diagram of brain showing afferent and efferent pathways.
Figure 7:
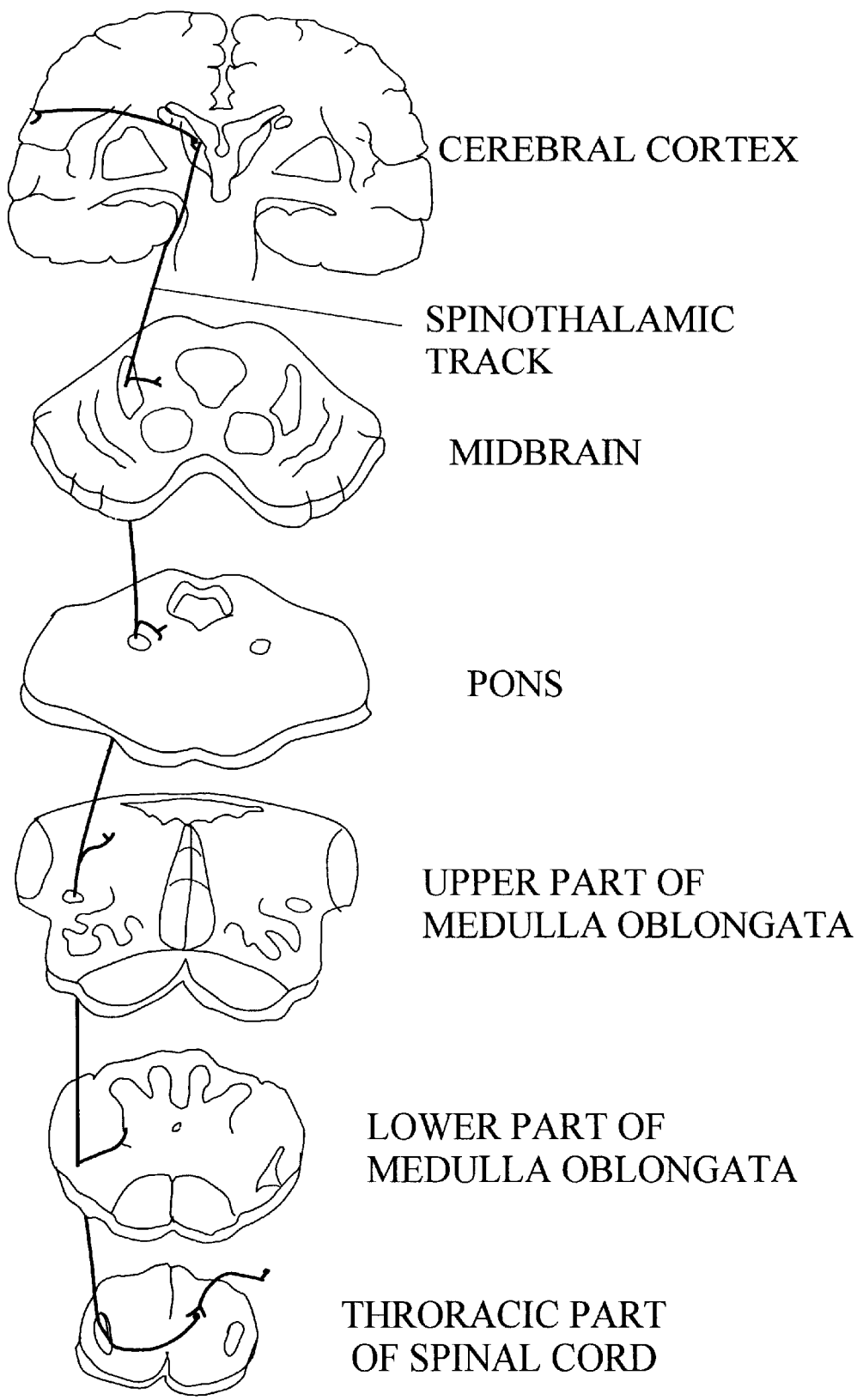
FIG. 7 is a schematic diagram showing pathways along the spinothalamic tract.
Figure 8:
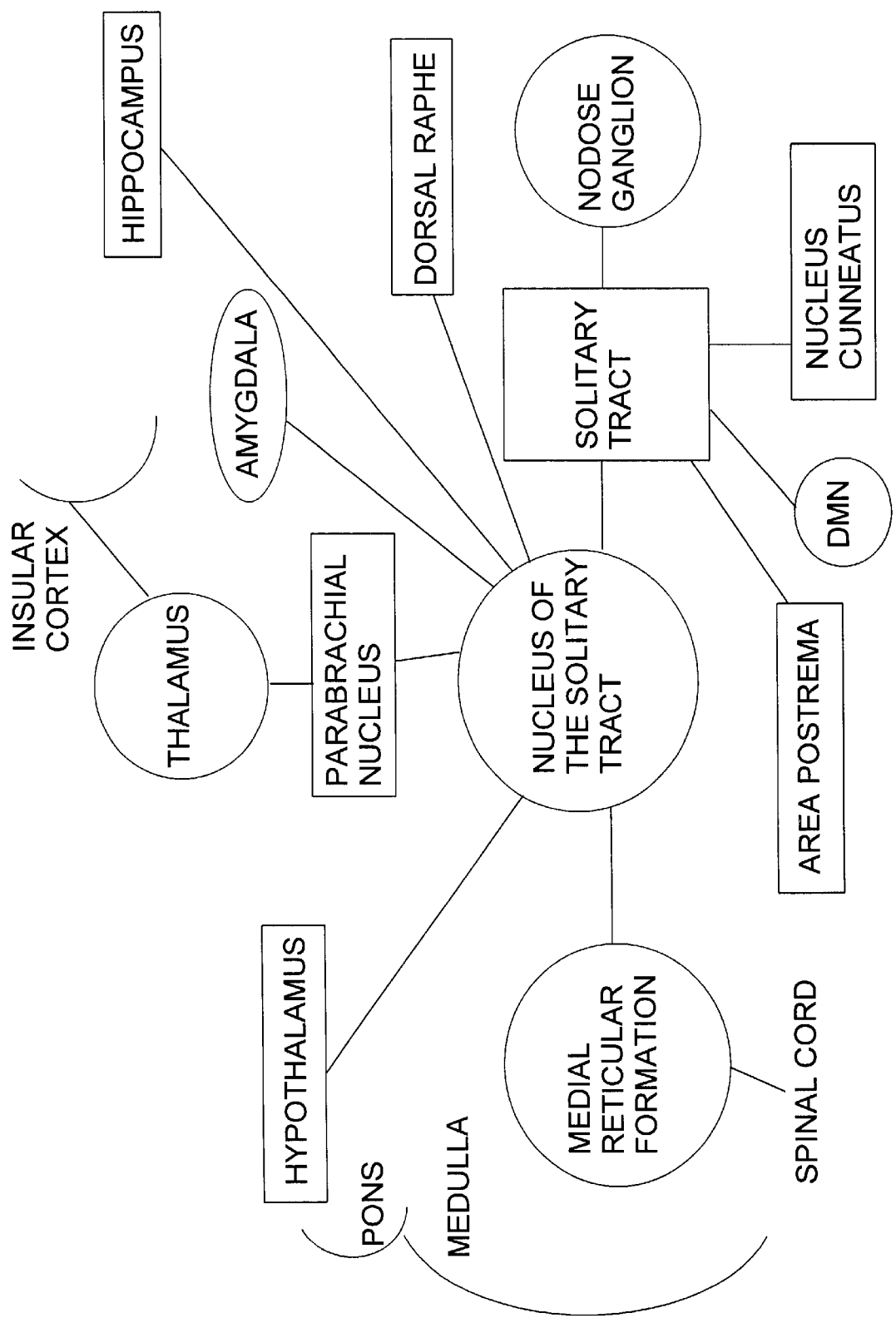
FIG. 8 is a schematic diagram showing relationship of Nucleus of the Solitary Track and how it relays information to other parts of the brain.
Figure 9:
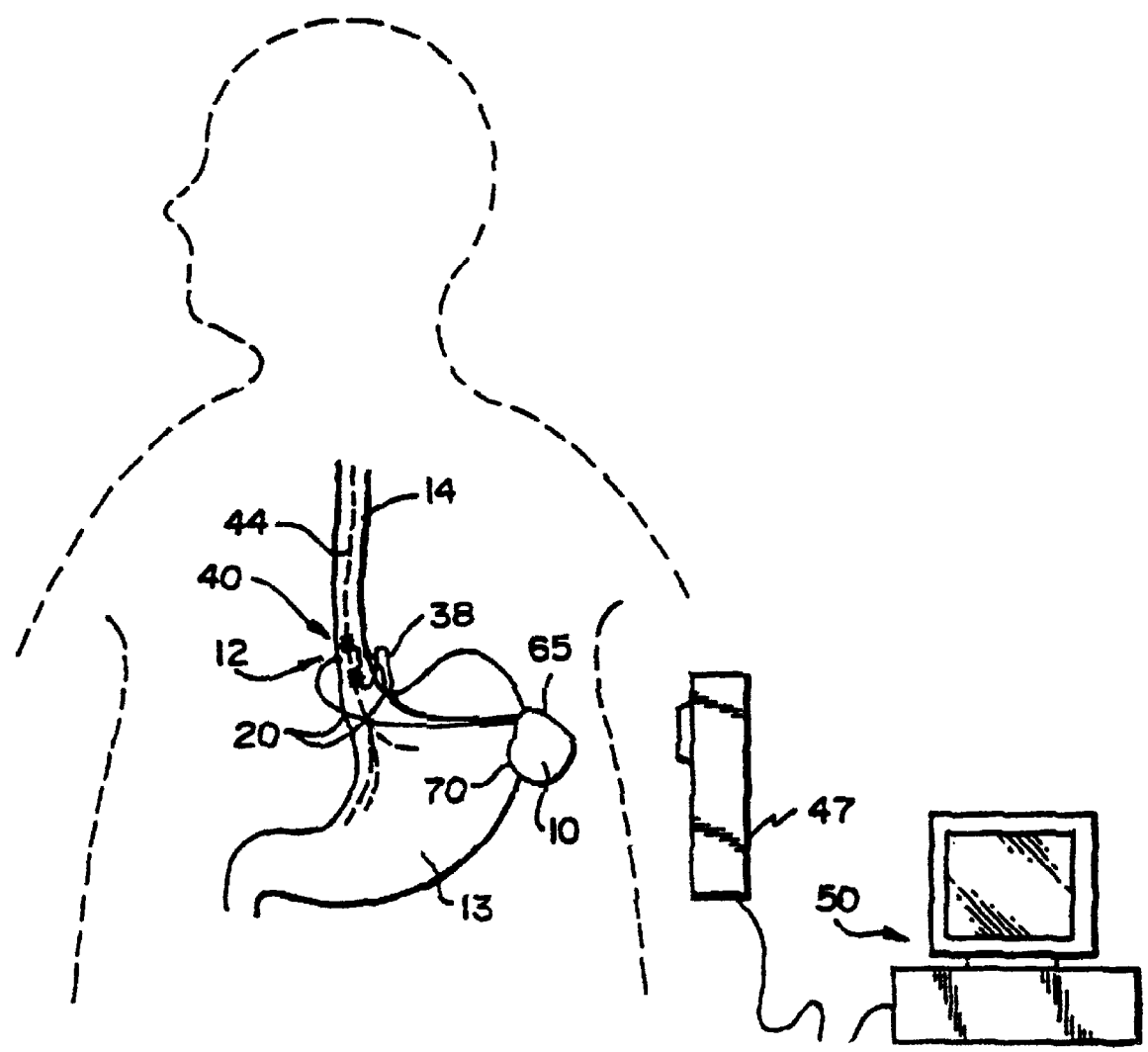
FIG. 9 is a prior art figure showing an implantable neurocybernetic osthesis, and a personnel computer based programmer.
Figure 10:
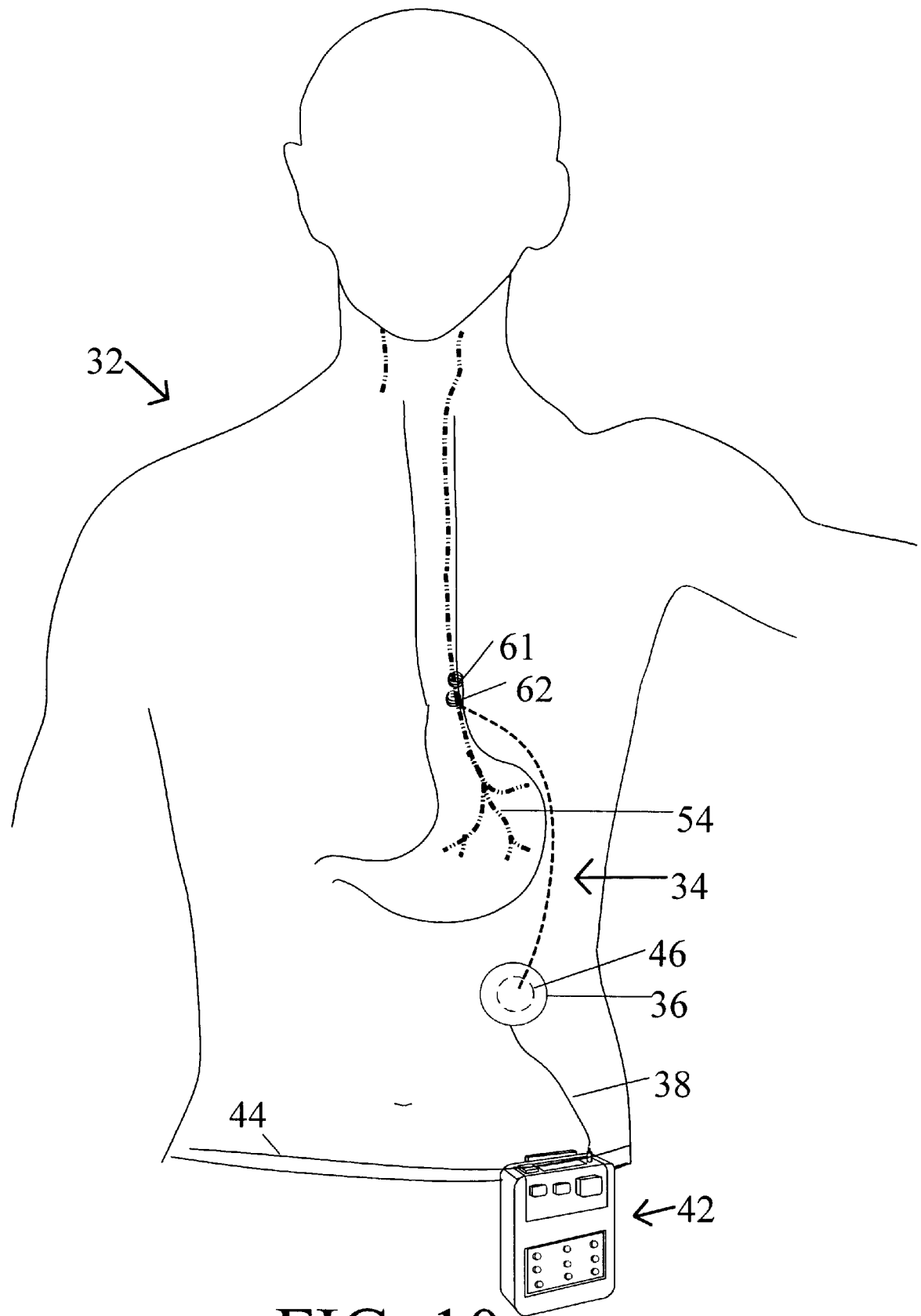
FIG. 10 is a schematic diagram of a patient with an implanted read receiver and an external stimulator with predetermined programs.

Referring now to FIG. 10, which shows a schematic diagram of a patient 32 with an implantable lead-receiver 34 and an external stimulator 42, clipped on to a belt 44 in this case. The external stimulator 42, may alternatively be placed in a pocket or other carrying device. The primary (external) coil 46 of the external stimulator 42 is inductively coupled to the secondary (implanted) coil 48 of the implanted lead-receiver 34. The implantable lead-receiver 34 has circuitry at the proximal end 49, and has two stimulating electrodes at the distal end 61, 62. The negative electrode (cathode) 61 is positioned towards the brain and the positive electrode (anode) 62 is positioned away from the brain. During the surgical implant procedure, the stimulating electrodes are tunneled subcutaneously and the spiral shaped electrodes are wrapped around the vagus nerve 54 which is surgically isolated from the carotid artery 56 and jugular vein 58. The incisions are surgically closed and the chronic stimulation process can begin when the tissues are healed from the surgery.

Figure 11:
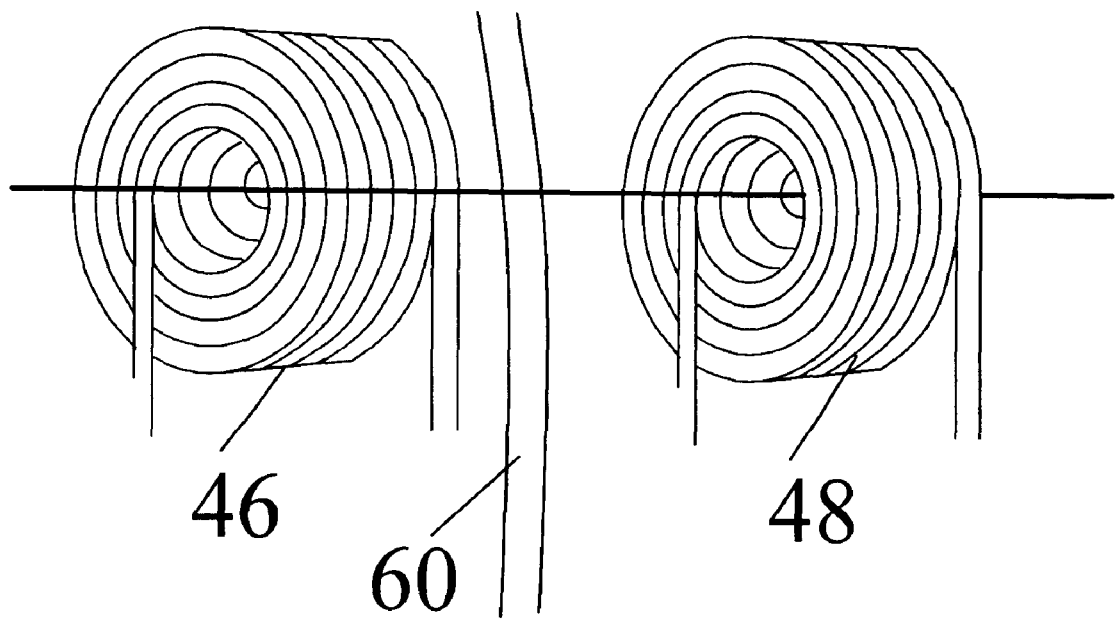
FIG. 11 is a diagram showing two coils along their axis in a configuration such that the mutual inductance would be maximum.

For therapy to commence, the primary (external) coil 46 is placed on the skin on top of the surgically implanted (secondary) coil 48. An adhesive tape is then placed on the skin 60 and external coil 46 such that the external coil 46, is taped firmly to the skin 60. For efficient energy transfer to occur, it is important that the primary (external) and secondary (internal) coils 46, 48 be positioned along the same axis and be optimally positioned relative to each other (FIG. 11). In the present embodiment, the external coil 46 is connected to proximity sensing circuitry 50. The correct positioning of the external coil 46 with respect to the internal coil 48 is indicated by turning "on" of a light emitting diode (LED) on the external stimulator 42.

Figure 12:
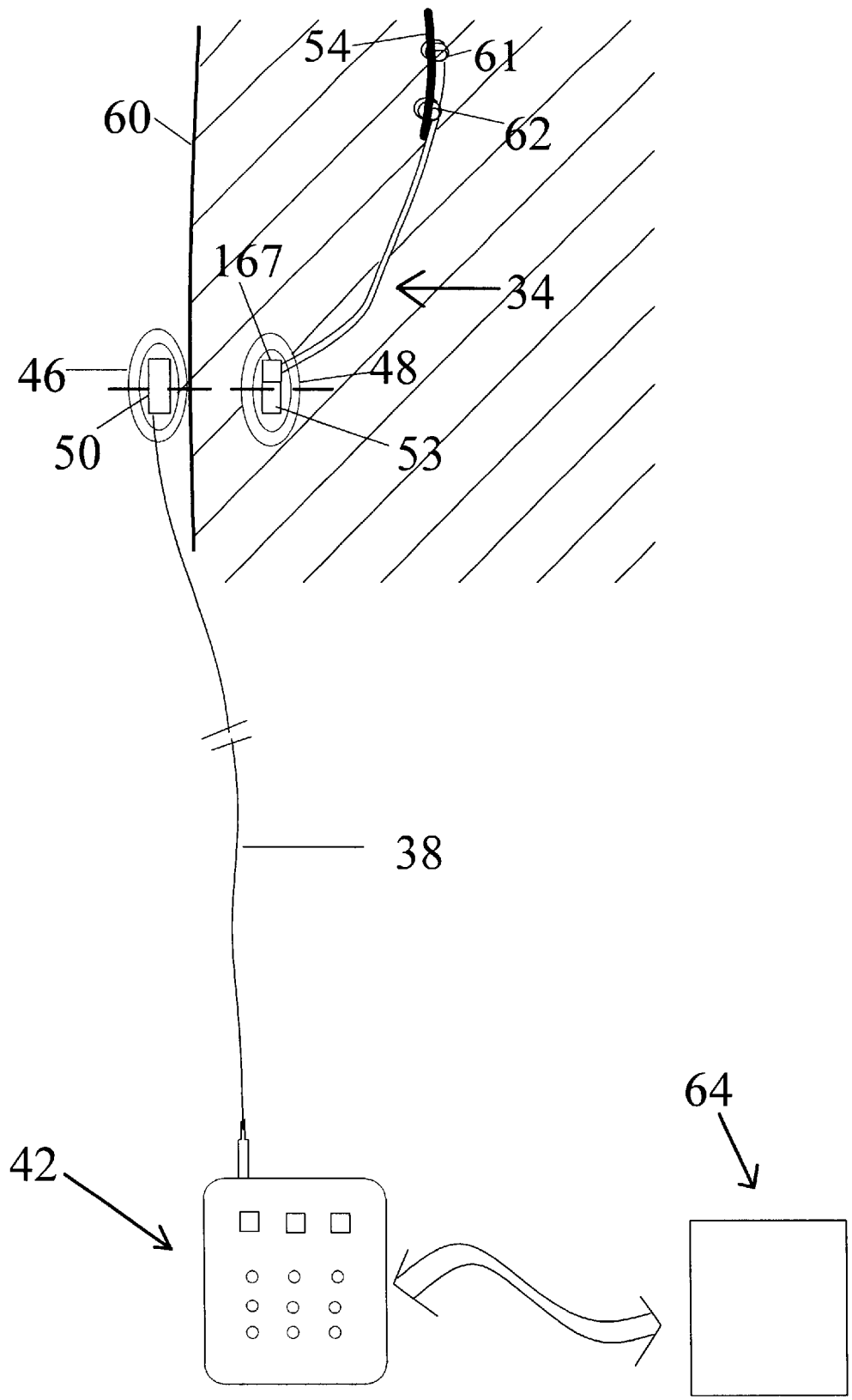
FIG. 12 shows external stimulator coupled to the implanted unit.

Optimal placement of the external (primary) coil 46 is done with the aid of proximity sensing circuitry incorporated in the system. Proximity sensing occurs utilizing a combination of external and implantable or internal components. The internal components contains a relatively small magnet composed of materials that exhibit Giant Magneto-Resistor (GMR) characteristics such as Samarium-cobalt, a coil, and passive circuitry. As shown in FIG. 12, the external coil 46 and proximity sensor circuitry 50 are rigidly connected in a convenient enclosure which is attached externally on the skin. The sensors measure the direction of the field applied from the magnet to sensors within a specific range of field strength magnitude. The dual sensors exhibit accurate sensing under relatively large separation between the sensor and the target magnet. As the external coil 46 placement is "fine tuned", the condition where the external (primary) coil 46 comes in optimal position, i.e. is located adjacent and parallel to the subcutaneous (secondary) coil 48, along its axis, is recorded and indicated by a light emitting diode (LED) on the external stimulator 42.

Figure 13:
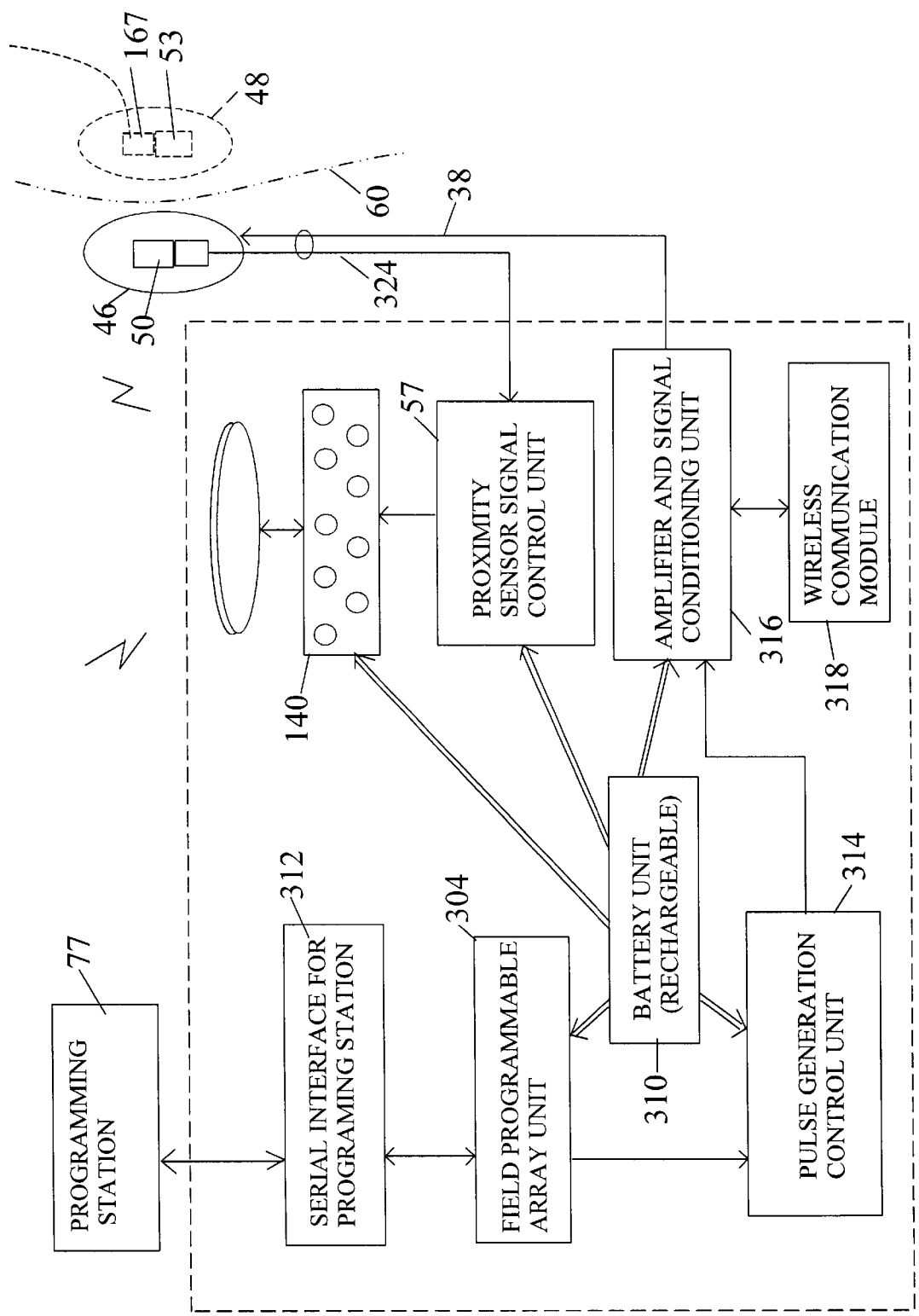
FIG. 13 is a top-level block diagram of the external stimulator and proximity sensing mechanism.

FIG. 13 shows an overall block diagram of the components of the external stimulator and the proximity sensing mechanism. The proximity sensing components are the primary (external) coil 46, supercutaneous (external) proximity sensors 198, 202 (FIG. 14) in the proximity sensor circuit unit 50, and a subcutaneous secondary coil 48 with a Giant Magneto Resister (GMR) magnet 53 associated with the proximity sensor unit. The proximity sensor circuit 50 provides a measure of the position of the secondary implanted coil 48. The signal output from proximity sensor circuit 50 is derived from the relative location of the primary and secondary coils 46, 48. The coil sub-assemblies consist of the coil and the associated electronic components, that are rigidly connected to the coil.

The proximity sensors (external) contained in the proximity sensor circuit 50 detect the presence of a GMR magnet 53, composed of Samarium Cobalt, that is rigidly attached to the subcutaneous secondary coil 48. The proximity sensors, are mounted externally as a rigid assembly and sense the actual separation between the coils, also known as the proximity distance. In the event that the distance exceeds the system limit, the signal drops off and an alarm sounds to indicate failure of the production of adequate signal in the secondary implanted circuit 167, as applied in the present embodiment of the device. This signal is provided to the location indicator LED 140.

Figure 14:
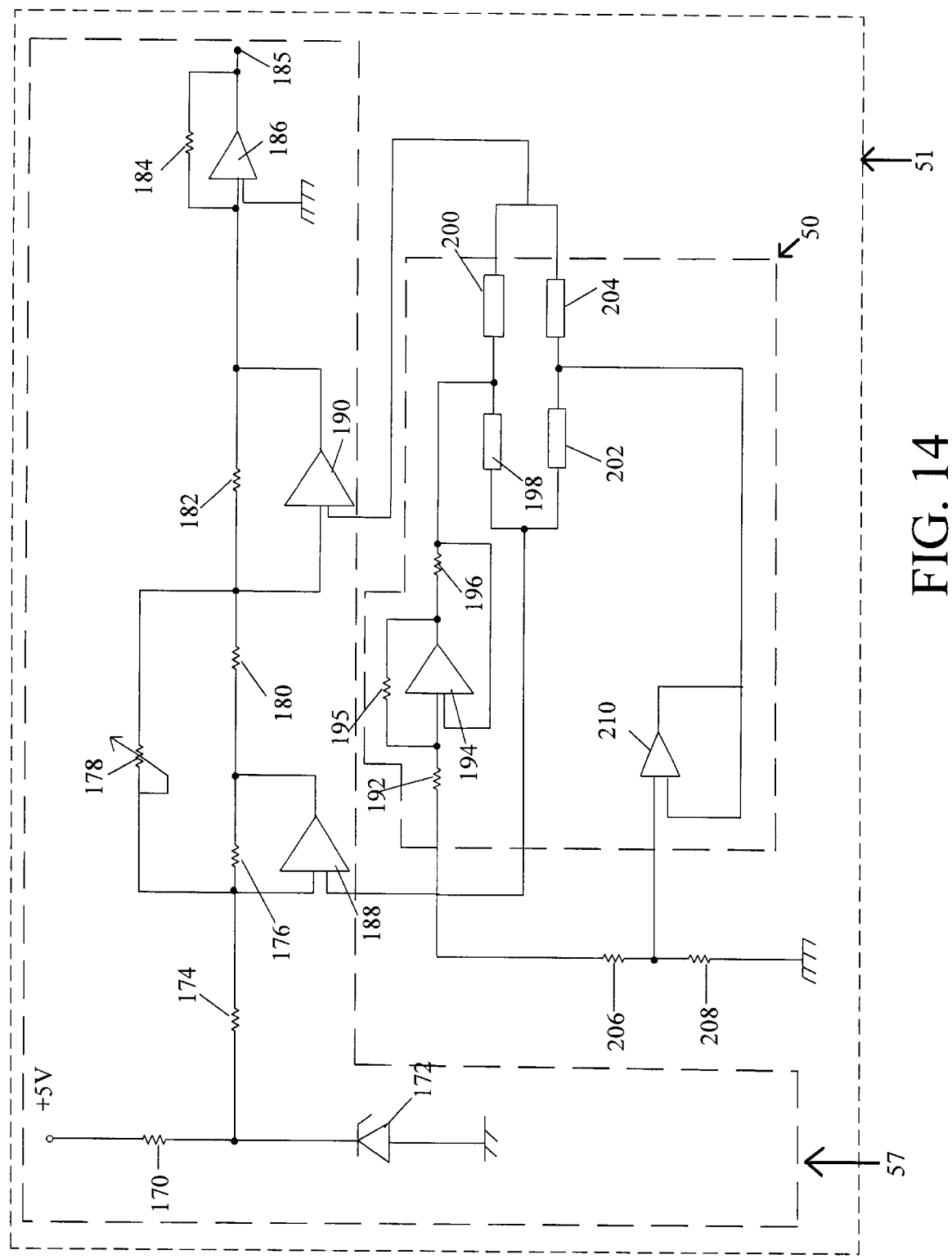
FIG. 14 is a diagram showing the proximity sensor circuitry.

FIG. 14 shows the circuit used to drive the proximity sensors 198, 202 of the proximity sensor circuit. The two proximity sensors 198, 202 obtain a proximity signal based on their position with respect to the implanted GMR magnet 53. This circuit also provides temperature compensation. The sensors 198, 202 are 'Giant Magneto Resistor' (GMR) type sensors packaged as proximity sensor unit 50. There are two components of the complete proximity sensor circuit 51. One component is mounted supercutaneously 50, and the other component, the proximity sensor signal control unit 57 is within the external stimulator 42. The resistance effect depends on the combination of the soft magnetic layer of magnet 53, where the change of direction of magnetization from external source can be large, and the hard magnetic layer, where the direction of magnetization remains unchanged. The resistance of this sensor varies along a straight motion through the curvature of the magnetic field. A bridge differential voltage is suitably amplified and used as the proximity signal.

The Siemens GMR B6 (Siemens Corp., Special Components Inc. New Jersey) is used for this function in the present embodiment. The maximum value of the peak-to-peak signal is observed as the external magnetic field becomes strong enough, at which point the resistance increases, resulting in the increase of the field-angle between the soft magnetic and hard magnetic material. The bridge voltage also increases. In this application, the two sensors 198, 202 are oriented orthogonal to each other.

The distance between the magnet and sensor is not relevant as long as the magnetic field is between 5 and 15 KA/m, and provides a range of distances between the sensors 198, 202 and the magnetic material 53. The GMR sensor registers the direction of the external magnetic field. A typical magnet to induce permanent magnetic field is approximately 15 by 8 by 5 mm$^3$, for this application and these components. However, the sensors 198, 202 are sensitive to temperature, such that the corresponding resistance drops as temperature increases. This effect is quite minimal until about 100° C. A full bridge circuit is used for temperature compensation, as shown in temperature compensation circuit 50 of FIG. 14. The sensors 198, 202 and a pair of resistors 200, 204 are shown as part of the bridge network for temperature compensation. It is also possible to use a full bridge network of two additional sensors in place of the resistors 200, 204.

The signal from either proximity sensor 198, 202 is rectangular if the surface of the magnetic material is normal to the sensor and is radial to the axis of a circular GMR device. This indicates a shearing motion between the sensor and the magnetic device. When the sensor is parallel to the vertical axis of this device, there is a fall off of the relatively constant signal at about 25 mm. separation. The GMR sensor combination varies its resistance according to the direction of the external magnetic field, thereby providing an absolute angle sensor. The position of the GMR magnet can be registered at any angle from 0 to 360 degrees.

The external stimulator shown in FIG. 13, with indicator unit 140 which is provided to indicate proximity distance or coil proximity failure (for situations where the patch containing the external coil 46, has been removed, or is twisted abnormally etc.). Indication is also provided to assist in the placement of the patch. In case of general failure, a red light with audible signal is provided when the signal is not reaching the subcutaneous circuit. The indicator unit 140 also displays low battery status. The information on the low battery, normal and out of power conditions will forewarn the user of the requirements of any corrective actions.

Figure 15:
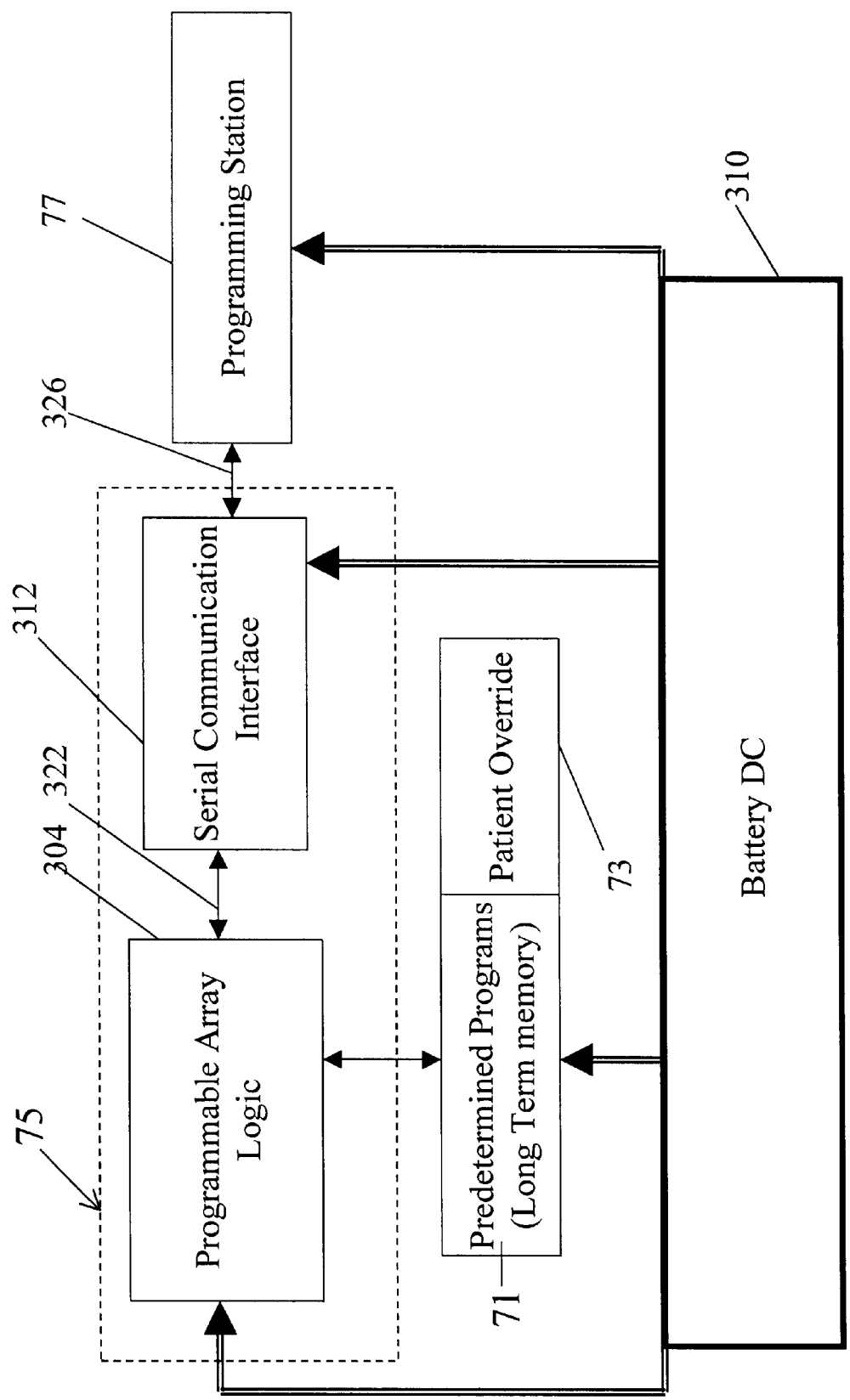
FIG. 15 is a block diagram of programmable array logic interfaced to the programming station.
Figure 16:
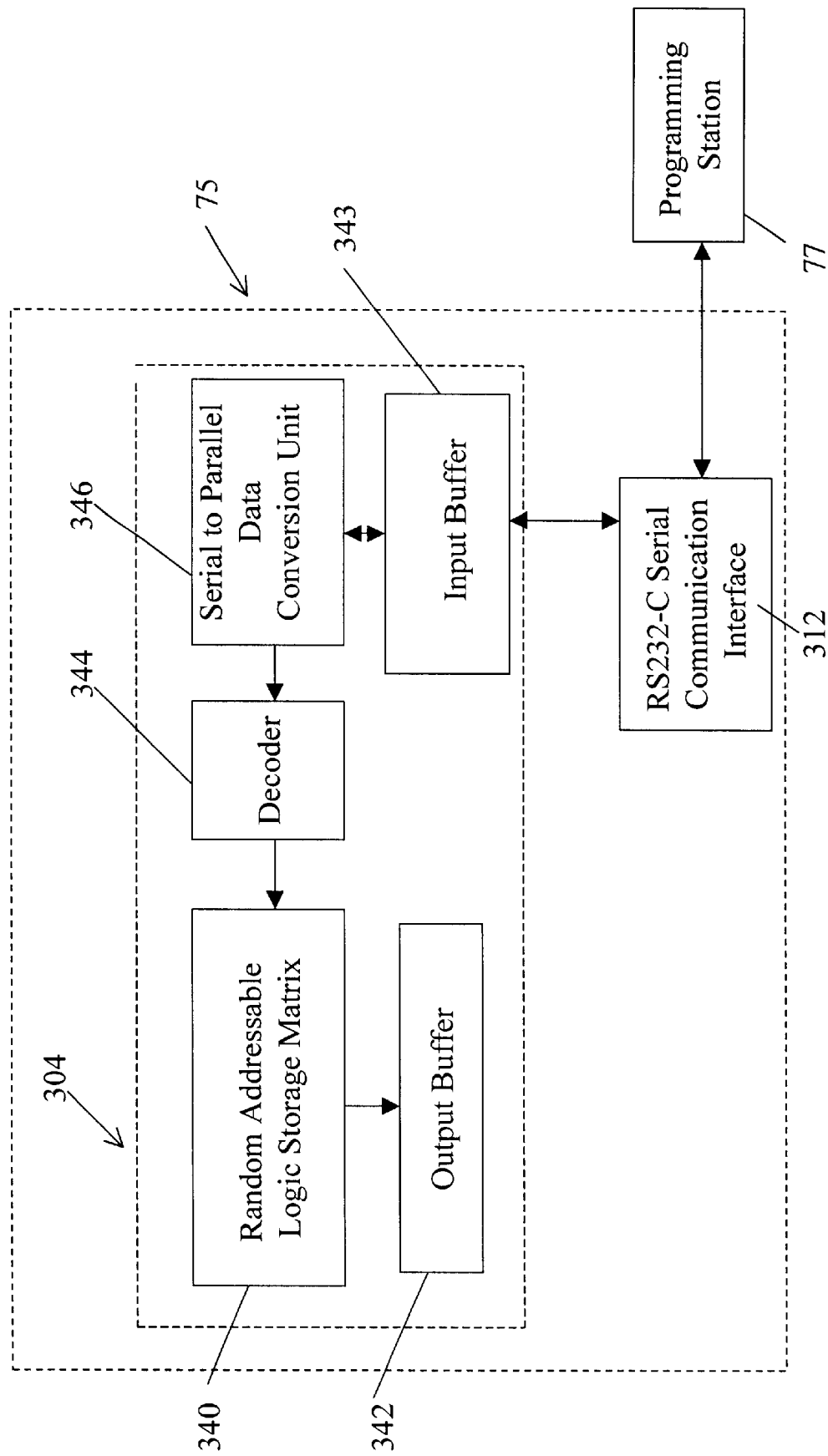
FIG. 16 is a block diagram showing details of programmable logic array unit.

As was shown in FIG. 13, the programmable parameters are stored in programmable logic unit 304. The predetermined programs stored in the external stimulator are capable of being modified through the use of a separate Programming Station 77. FIG. 15 shows the Programmable Array Logic Unit 304 and interface 10 unit 312 interfaced to the programming station 77. The programming station 77 can be used to load new programs, change the predetermined programs, or the program parameters for various stimulation programs. The programming station is connected to the Programmable Array Unit 75, shown in FIG. 16 (comprising programmable array logic 304 and interface unit 312) with an RS232-C serial connection. The main purpose of the serial line interface is to provide an RS232-C standard interface. This method enables any portable computer with a serial interface to communicate and program the parameters for storing the various programs. The serial communication interface receives the serial data, buffers this data and converts it to a 16 bit parallel data. The Programmable Array Logic 304 component of Programmable Array Unit 75 receives the parallel data bus and stores or modifies the data into a random access matrix 340 (FIG. 16). This array of data also contains special logic and instructions along with the actual data. These special instructions also provide an algorithm for storing, updating and retrieving the parameters from long-term memory. The Programmable Logic Array Unit 304, interfaces with Long Term Memory to store the predetermined programs 71. All the previously modified programs can be stored here for access at any time, as well as, additional programs can be locked out for the patient. The programs consist of specific parameters and each unique program will be stored sequentially in long-term memory. A battery unit 310 is present to provide power to all the components shown above. The logic for the storage and decoding is stored in the Random Addressable Storage Matrix (RASM) 340 (FIG. 16).

FIG. 16 shows greater details for the Programmable Logic Array Unit 304. The Input Buffer block 343 is where the serial data is stored in temporary register storage. This accumulation allows for the serial to parallel conversion to occur. The serial to 16 bit parallel block 346 sets up 16 bits of data, as created from the RS232-C serial data. This parallel data bus will communicate the data and the address information. The decoder block 344 decodes address information for the Random Addressable Logic Storage Matrix 340 from which to access the data i.e. programmer parameters. The Output Buffer 342 provides an interface to the Long Term Memory 71.

Figure 17:
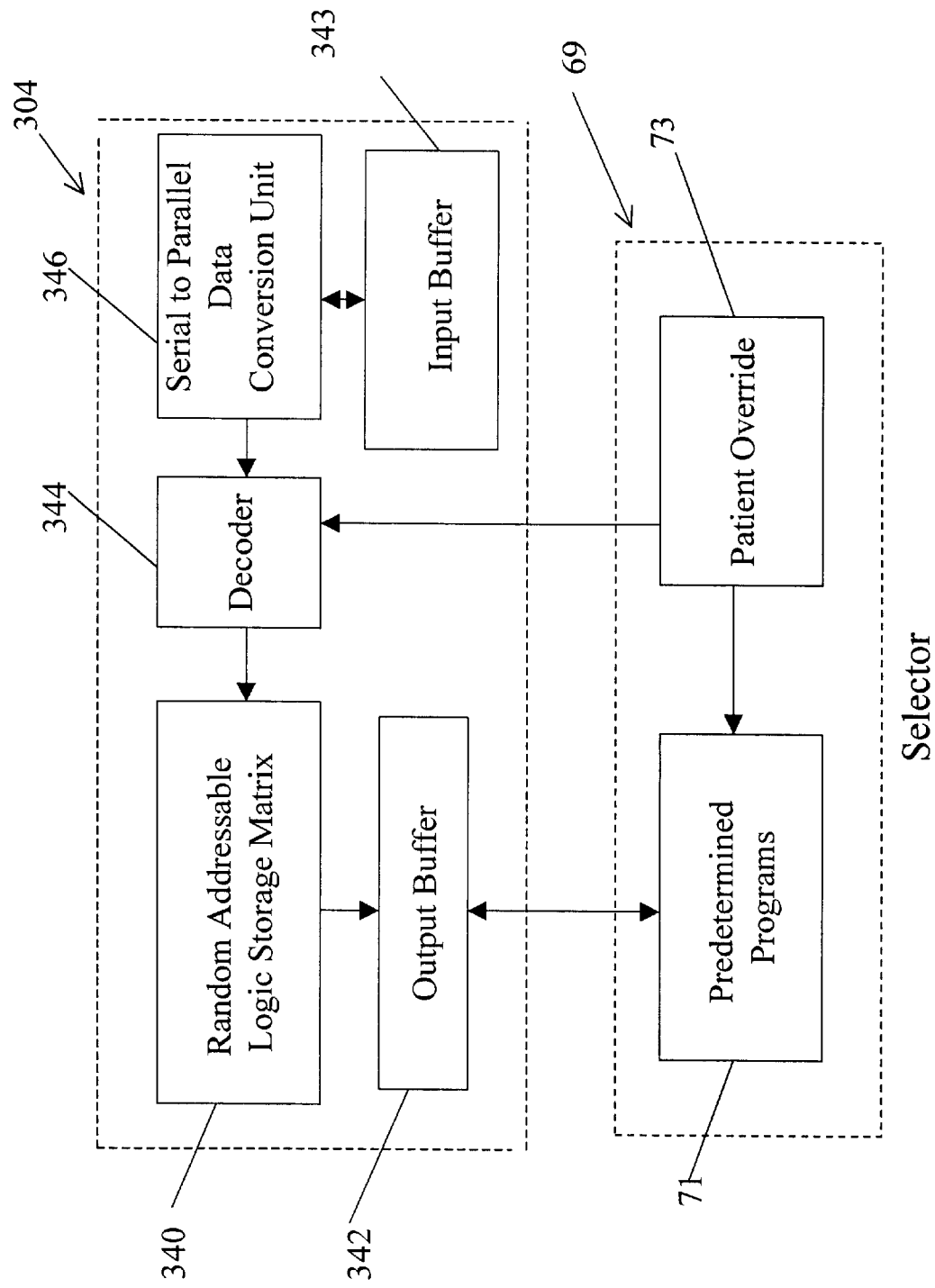
FIG. 17 is a diagram showing details of the interface between the programmable array logic and interface unit.

FIG. 17 shows schematically the details of the interface between the Programmable Array Logic 304 and Interface Unit 312 which is connected to the Predetermined Programs block (Long Term Memory) 71. The patient override 73 is essentially a control scheme for initializing or starting a program at any intermediate point. The Programmable array provides a reconfigurable mechanism to store data and associated instructions for the programs. It supports adding, modifying or retrieving the data from a Random Addressable Logic Storage Matrix 340. This is also a widely accepted scheme for treating "flexible" logic description and control. It is flexible by providing the ability to reprogram and even redesign existing programs previously installed as predetermined programs. It allows the manufacturer or authorized user to create, and modify the programs for execution.

Figure 18:
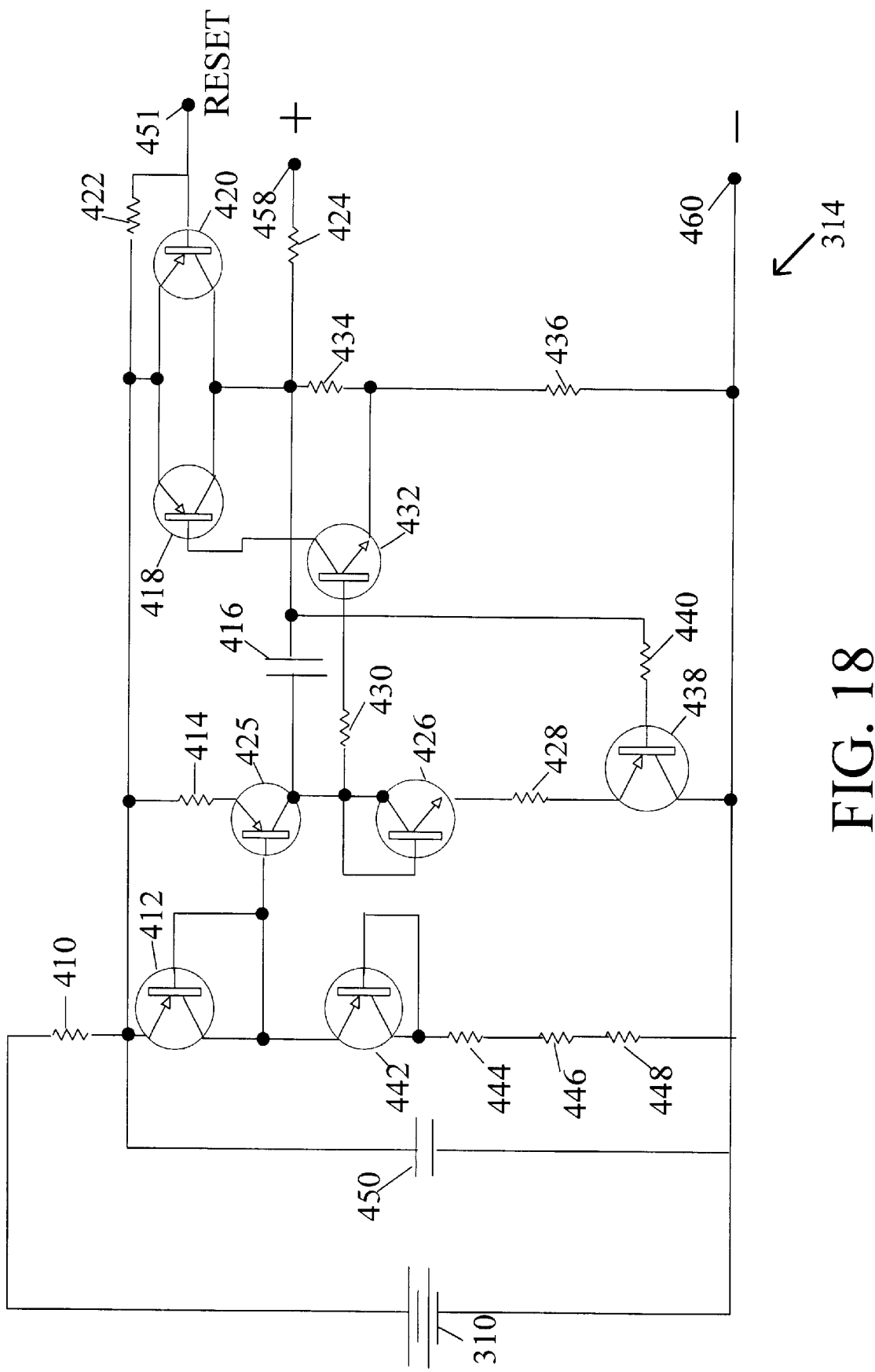
FIG. 18 is a diagram showing the circuitry of the pulse generator.

The pulse generator circuitry, shown schematically in FIG. 18, exhibits typical multivibrator functionality. This circuit produces regularly occurring pulses where the amplitude, pulse width and frequency is adjustable. The battery 310 is the main external power source for this circuit. The capacitor 450 is connected in parallel with the battery 310. The combination of transistors 412, 442 and 425, and resistors 410, 444, 446 and 448 acts as a constant current source generated at the collector of transistor 426. The transistor 412 has collector connected to the emitter of transistor 442 and base of transistor 425. The transistors 412 and 442 are connected to provide a constant voltage drop. Likewise, transistor 426 also acts as a diode with a resistor 428 connected in series and further connected to the negative terminal of the line at terminal 460. Capacitor 416 provides timing characteristics and its value helps determine pulse width and pulse frequency. The output of the oscillator appears at terminal 458.

Initially, the capacitor 416 gets charged with current from the path of resistor 434 and 436 while all the transistors are turned off. As the capacitor charges up transistor 432 will become forward biased and current will flow via resistors 430 and 436 from the base to emitter resistors. This action turns on the transistor 418 and the positive voltage from the power supply 310 is made available at the base of transistor 438 through resistor 440. This results in the transistor 438 getting turned on. The conduction of transistor 438 causes capacitor 416 to discharge. The time constant for the charge and discharge of capacitor 416 is determined by value of the resistors 428 and 440 and capacitor 416. After the time constant, transistor 432 turns off, and this in turn turns off transistors 438 and 418. A reset mechanism for this multivibrator can be provided by setting a positive voltage, for example 2.5 volts, to the base of transistor 420. This positive increase in voltage turns on transistor 420 followed by transistor 438. The turning on of transistor 438 discharges the capacitor 416 and the reset operation is complete.

Conventional microprocessor and integrated circuits are used for the logic, control and timing circuits. Conventional bipolar transistors are used in radio-frequency oscillator, pulse amplitude ramp control and power amplifier. A standard voltage regulator is used in low-voltage detector. The hardware and software to deliver the pre-determined programs is well known to those skilled in the art.

Figure 19:
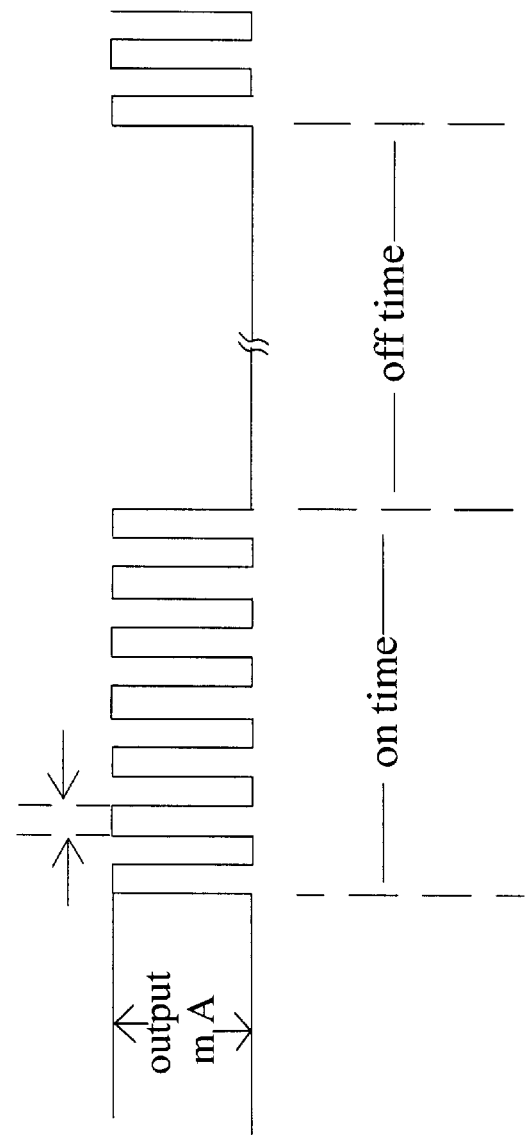
FIG. 19 shows the pulse train to be transmitted to the implant unit.
Figure 20:
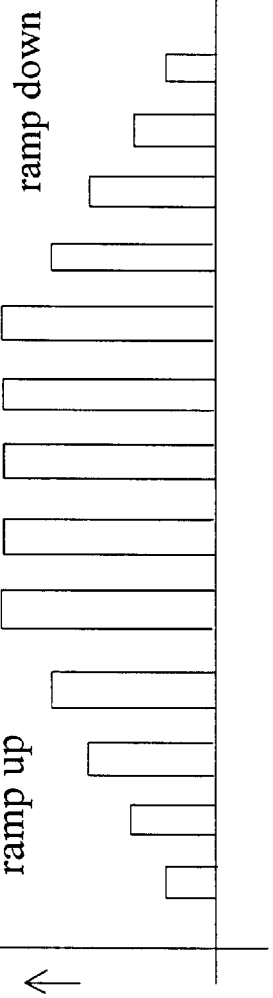
FIG. 20 shows the ramp-up and ramp-down characteristic of the pulse train.

The pulses delivered to the nerve tissue for stimulation therapy are shown graphically in FIG. 19. As shown in FIG. 20, for patient comfort when the electrical stimulation is turned on, the electrical stimulation is ramped up and ramped down, instead of abrupt delivery of electrical pulses.

The number of predetermined programs can be any number, say 100, and such a number is considered within the scope of the invention. For patient convenience, less than 20 programs are practical. One embodiment contains nine predetermined programs.

In one arrangement, the predetermined programs are arranged in such a way that the aggressiveness of the therapy increases from program #1 to Program #9. Thus the first three programs provide the least aggressive therapy, and the last three programs provide the most aggressive therapy.

The following are examples of least aggressive therapy.
Program #1
  1.0 mA current output, 0.2 msec pulse width, 15 Hz frequency, 15 sec on-time, 1.0 min off-time, in repeating cycles.
Program #2
  1.5 mA current output, 0.3 msec pulse width, 20 Hz frequency, 20 sec on-time, 2.0 min off-time, in repeating cycles.

The following are examples of intermediate level of therapy.
Program #5
  2.0 mA current output, 0.3 msec pulse width, 25 Hz frequency, 20 sec on-time, 1.0 min off-time, in repeating cycles.
Program #6
  2.0 mA current output, 0.4 msec pulse width, 25 Hz frequency, 30 sec on-time, 1.0 min off-time, in repeating cycles.

The following are examples of most aggressive therapy.
Program #8
  2.5 mA current output, 0.3 msec pulse width, 30 Hz frequency, 40 sec on-time, 1.5 min off-time, in repeating cycles.
Program #9
  3.0 mA current output, 0.5 msec pulse width, 30 Hz frequency, 30 sec on-time, 1.0 min off-time, in repeating cycles.

The majority of patients will fall into the category that require an intermediate level of therapy, such as program #5. The above are examples of the predetermined programs that are delivered to the vagus nerve. The actual parameter settings for any given patient may deviate somewhat from the above. As shown schematically in FIG. 13, new predetermined programs can be loaded into the external stimulator 42.

In one embodiment, the external stimulator can also have a telecommunications module, as described in a co-pending application, and summarized here for reader convenience. The telecommunications module has two-way communications capabilities.

Figure 21:
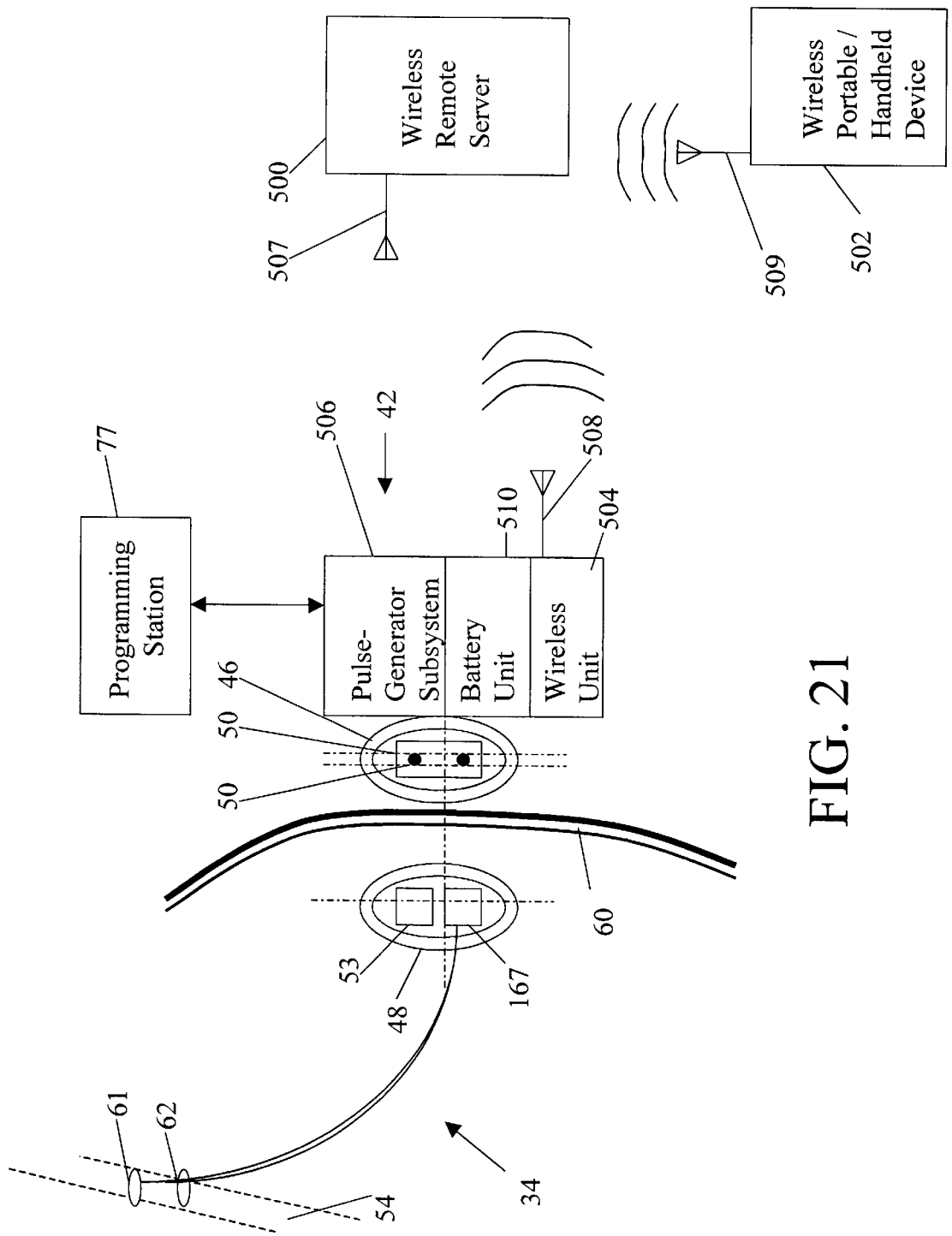
FIG. 21 is an overall schematic diagram of the external stimulator, showing wireless communication.

FIG. 21 shows conceptually the communication between the external stimulator 42 and a remote hand-held computer. A desktop or laptop computer can be a server 500 which is situated remotely, perhaps at a physician's office or a hospital. The stimulation parameter data can be viewed at this facility or reviewed remotely by medical personnel on a hand-held personal data assistant (PDA) 502, such as a "palm-pilot" from PALM corp. (Santa Clara, Calif.), a "Visor" from Handspring Corp. (Mountain view, Calif.) or on a personal computer (PC) available from numerous vendors. The physician or appropriate medical personnel, is able to interrogate the external stimulator 42 device and know what the device is currently programmed to, as well as, get a graphical display of the pulse train. The wireless communication with the remote server 500 and hand-held PDA 502 would be supported in all geographical locations within and outside the United States (US) that provides cell phone voice and data communication service. The pulse generation parameter data can also be viewed on the hand-held devices (PDA) 502.

The telecommunications component of this invention uses Wireless Application Protocol (WAP). The Wireless Application Protocol (WAP) is a set of communication protocols standardizing Internet access for wireless devices.

While previously, manufacturers used different technologies to get Internet on hand-held devices, with WAP devices and services interoperate. WAP promotes convergence of wireless data and the Internet. The WAP programming model is heavily based on the existing Internet programming model, and is shown schematically in FIG. 22. Introducing a gateway function provides a mechanism for optimizing and extending this model to match the characteristics of the wireless environment. Over-the-air traffic is minimized by binary encoding/decoding of Web pages and readapting the Internet Protocol stack to accommodate the unique characteristics of a wireless medium such as call drops. Such features are facilitated with WAP.

Figure 22:
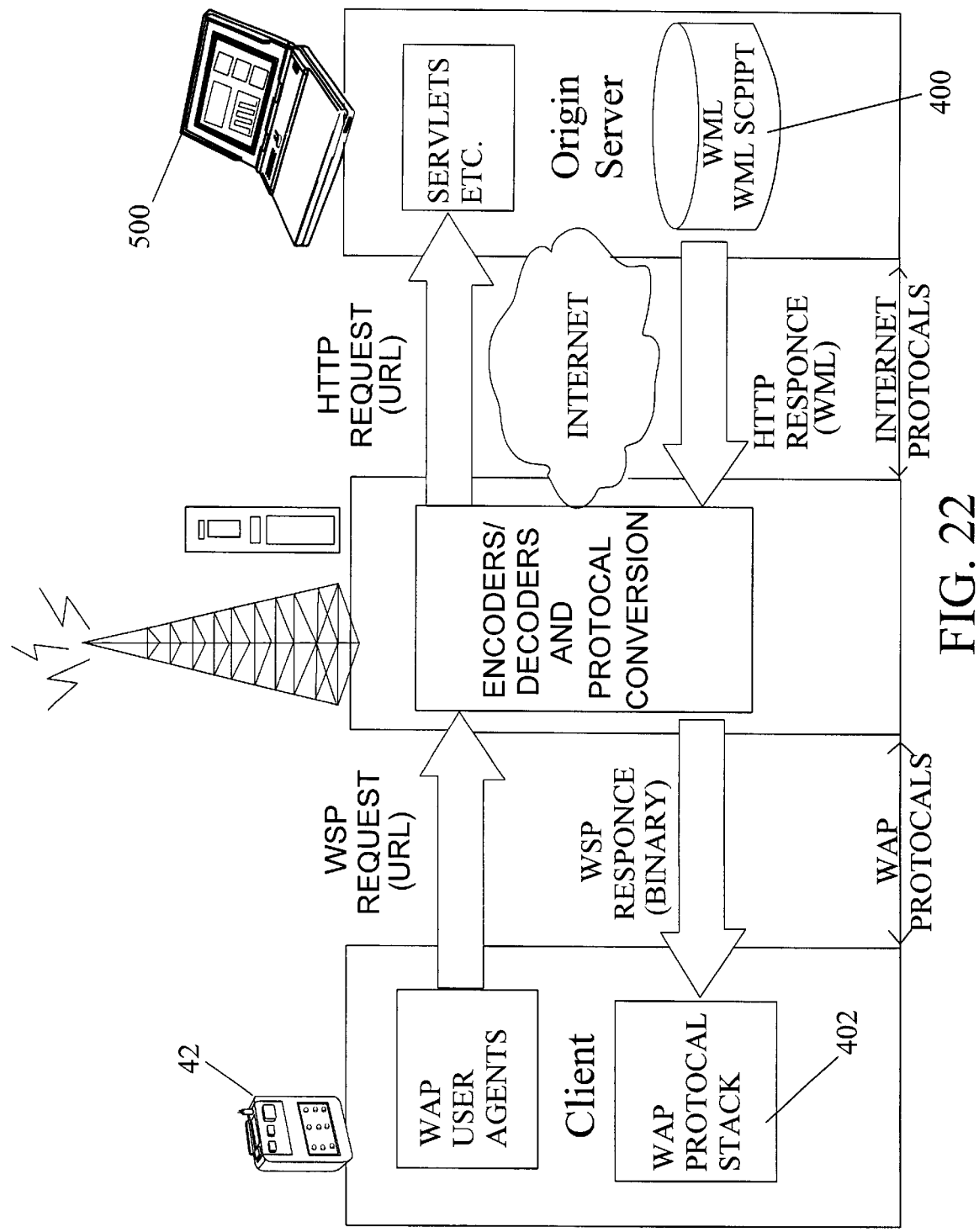
FIG. 22 is a schematic diagram showing application of Wireless Application Protocol (WAP).

The key components of the WAP technology, as shown in FIG. 22, includes 1) Wireless Mark-up Language (WML) 400 which incorporates the concept of cards and decks, where a card is a single unit of interaction with the user. A service constitutes a number of cards collected in a deck. A card can be displayed on a small screen. WML supported Web pages reside on traditional Web servers. 2) WML Script which is a scripting language, enables application modules or applets to be dynamically transmitted to the client device and allows the user interaction with these applets. 3) Microbrowser, which is a lightweight application resident on the wireless terminal that controls the user interface and interprets the WML/WMLScript content. 4) A lightweight protocol stack 402 which minimizes bandwidth requirements, guaranteeing that a broad range of wireless networks can run WAP applications. The protocol stack of WAP can comprise a set of protocols for the transport (WTP), session (WSP), and security (WTLS) layers. WSP is binary encoded and able to support header caching, thereby economizing on bandwidth requirements. WSP also compensates for high latency by allowing requests and responses to be handled asynchronously, sending before receiving the response to an earlier request. For lost data segments, perhaps due to fading or lack of coverage, WTP only retransmits lost segments using selective retransmission, thereby compensating for a less stable connection in wireless. The above mentioned features are industry standards adopted for wireless applications and greater details have been publicized, and well known to those skilled in the art.

In this embodiment, two modes of communication are possible. In the first, the server initiates an upload of the actual parameters being applied to the patient, receives these from the stimulator, and stores these in its memory, accessible to the authorized user as a dedicated content driven web page. The physician or authorized user can make alterations to the actual parameters, as available on the server, and then initiate a communication session with the stimulator device to download these parameters.

The physician is also able to set up long-term schedules of stimulation therapy for their patient population, through wireless communication with the server. The server in turn communicates these programs to the neurostimulator. Each schedule is securely maintained on the server, and is editable by the physician and can get uploaded to the patient's stimulator device at a scheduled time. Thus, therapy can be customized for each individual patient. Each device issued to a patient has a unique identification key in order to guarantee secure communication between the wireless server 502 and stimulator device 42.

The second mode of communication is the ability to remotely interrogate and monitor the stimulation therapy on the physician's handheld (PDA) 502.

Figure 23:
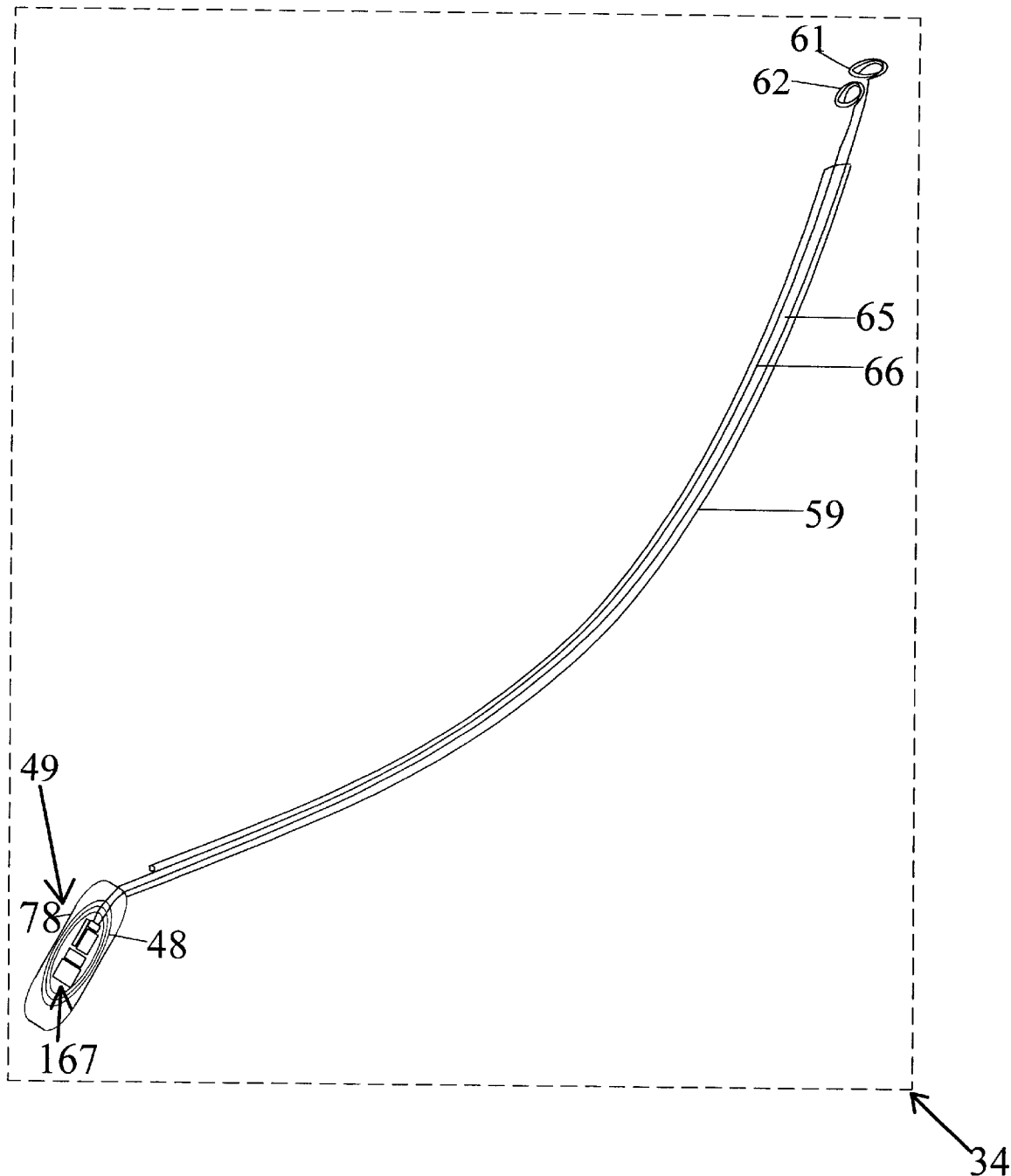
FIG. 23A is a diagram of the implanted lead receiver.
FIG. 23B is a schematic diagram of the proximal end of the lead receiver implanted lead receiver.
Figure 23:
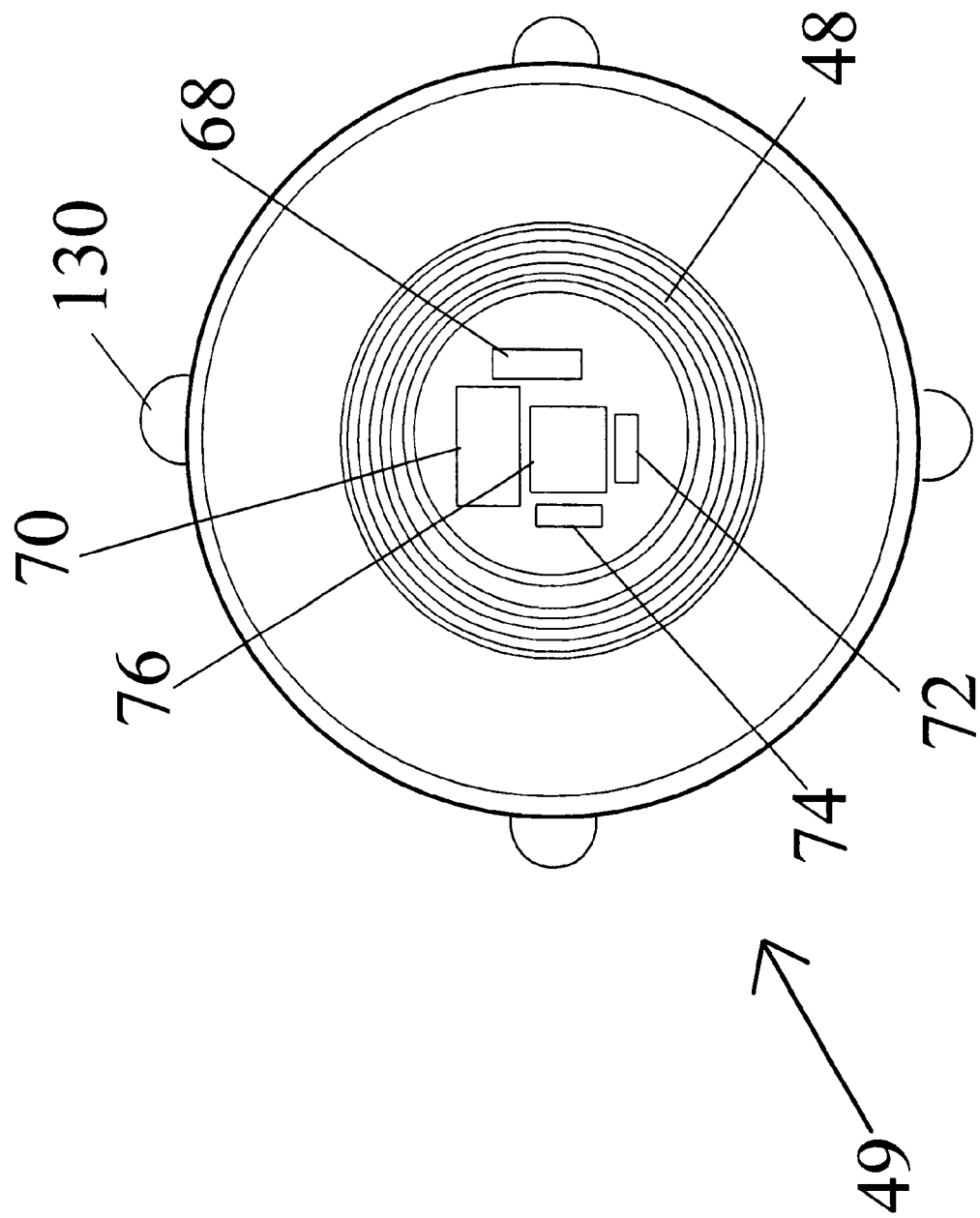

Moving now to the implantable portion of the system, FIG. 23A shows a diagram of the implanted lead-receiver 34, and FIG. 23B shows a diagram of the proximal end 49 of the lead-receiver 34. The proximal end 49 is a relatively flat portion and contains the electrical components on a printed circuit board. The distal end has the two spiral electrodes 61 and 62 for stimulating the nerve. The passive circuitry and electrodes are connected by electrically insulated wire conductors running within the lead body 59. The lead body 59 is made of reinforced medical grade silicone in the presently preferred embodiment.

Figure 24:
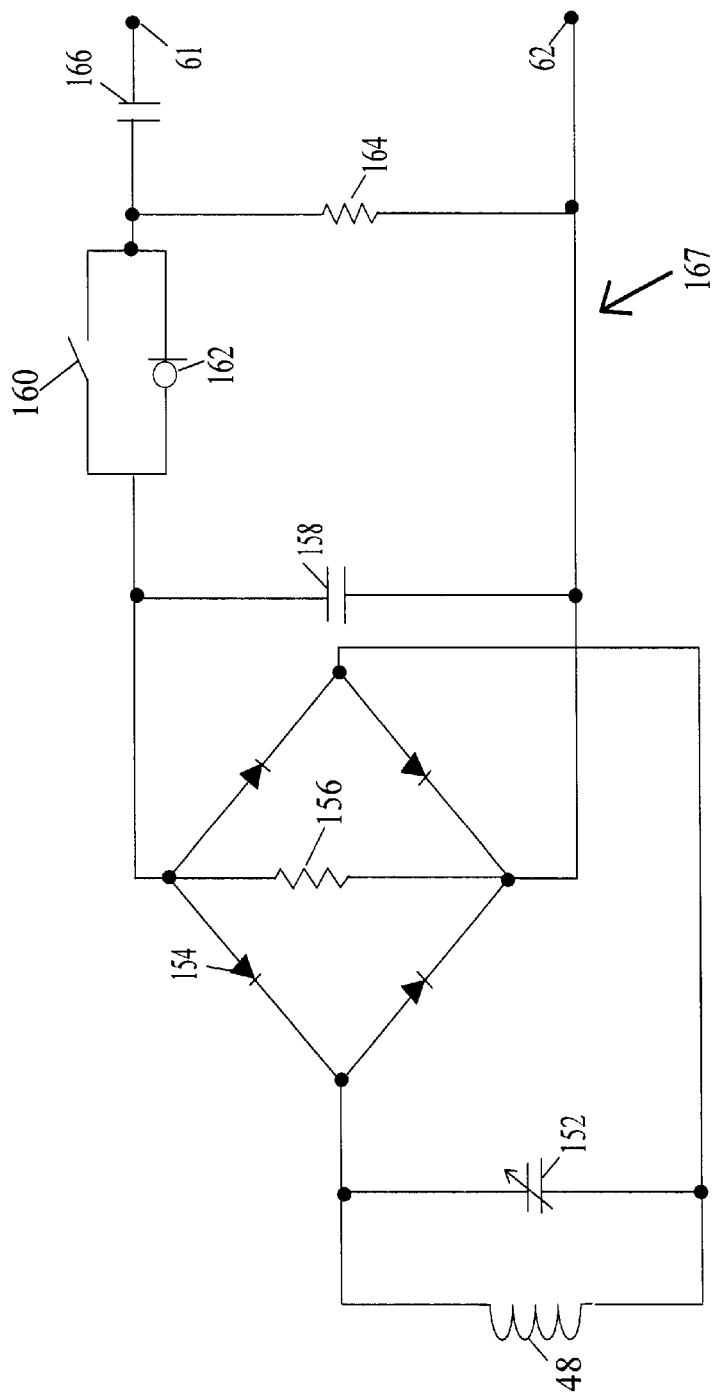
FIG. 24 is a schematic of the passive circuitry in the implanted lead-receiver.

The circuitry contained in the proximal end 49 of the implantable lead-receiver 34 is shown schematically in FIG. 24, for the presently preffered embodiment. In this embodiment, the circuit uses all passive components. Approximately 25 turn copper wire of 30 gauge, or comparable thickness, is used for the primary coil 46 and secondary coil 48. This wire is concentrically wound with the windings all in one plane. The frequency of the pulse-waveform delivered to the implanted coil 48 can vary and so a variable capacitor 152 provides ability to tune secondary implanted circuit 167 to the signal from the primary coil 46. The pulse signal from secondary (implanted) coil 48 is rectified by the diode bridge 154 and frequency reduction obtained by capacitor 158 and resistor 164. The last component in line is capacitor 166, used for isolating the output signal from the electrode wire. The return path of signal from cathode 61 will be through anode 62 placed in proximity to the cathode 61 for "Bipolar" stimulation. In the current embodiment bipolar mode of stimulation is used, however, the return path can be connected to the remote ground connection (case) of implantable circuit 167, providing for much larger intermediate tissue for "Unipolar" stimulation. The "Bipolar" stimulation offers localized stimulation of tissue compared to "Unipolar" stimulation and is therefore, used in the current embodiment. Unipolar stimulation is more likely to stimulate skeletal muscle in addition to nerve stimulation. The implanted circuit 167 in this embodiment is passive, so a battery does not have to be implanted. It is however possible to implant a battery source for use of active component logic in the implant.

Figure 25:
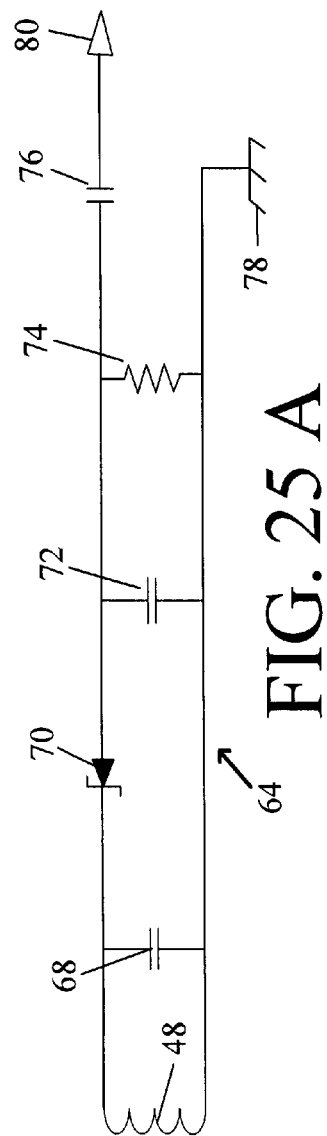
FIG. 25A is a schematic of an alternative embodiment of the implanted lead-receiver.
FIG. 25B is another alternative embodiment of the implanted lead-receiver.
Figure 25:
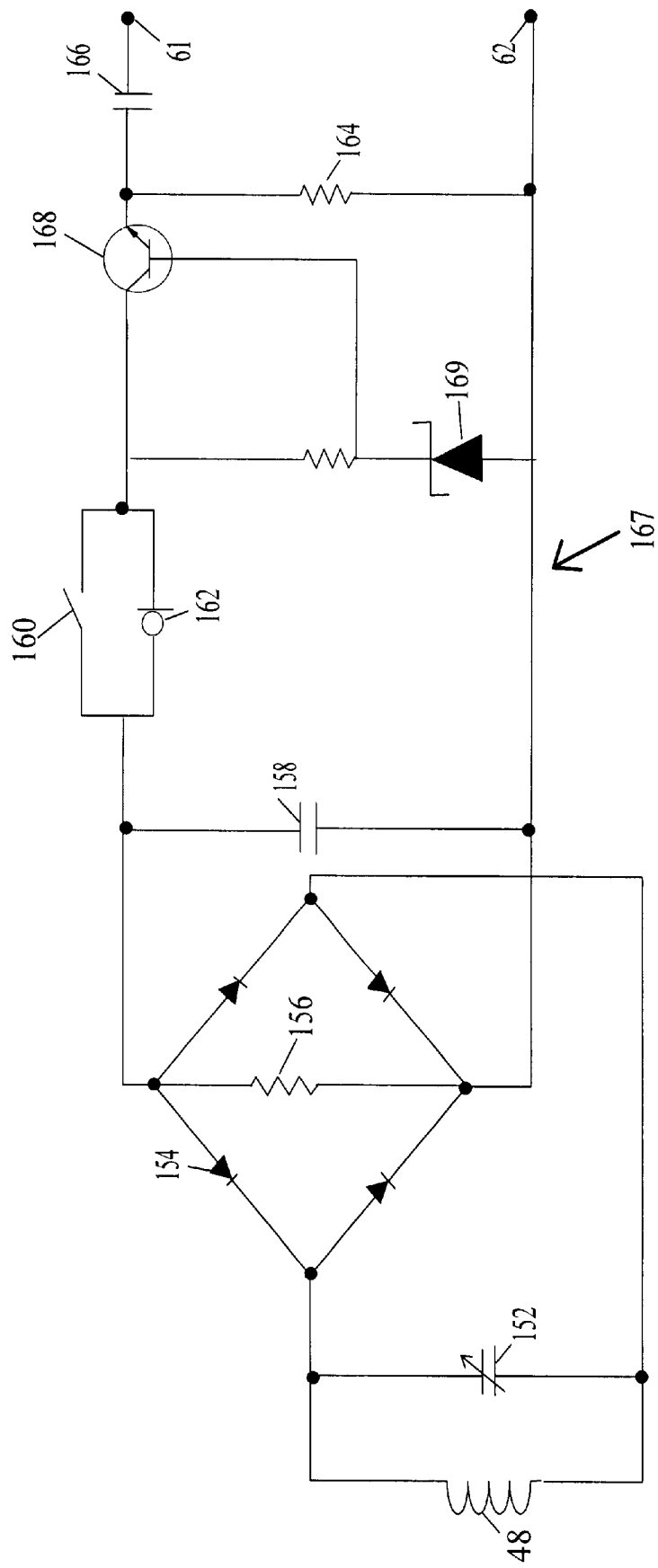

The circuitry shown in FIGS. 25A and 25B can be used as an alternative, for the implanted lead-receiver. The circuitry of FIG. 25A is a slightly simpler version, and circuitry of FIG. 25B contains a conventional NPN transistor 168 connected in an emitter-follower configuration.

The fabrication of the lead-receiver 34 is designed to be modular. Thus, several different combinations of the components can be packaged without significantly altering the functionality of the device. As shown in FIG. 23A, the lead-receiver 34 components are the proximal end 49 containing coil 48, electrical circuitry 167, and case 78. The lead body 59 containing the conductor 65,66 and the distal end has two electrodes cathode 61 and anode 62. In the modular design concept, several design variables are possible, as shown in the table below.

Table of lead-receiver design variables

| Circuitry | Lead body-Lumens | Lead body-Insulation Materials | Lead-Coating | Conductor (connecting proximal and distal ends) | Electrode - Material | Electrode - Type |
|---|---|---|---|---|---|---|
| Bipolar | | Polyurethane | | Alloy of Nickel-Cobalt | Pure Platinum | Standard ball electrode |
| Unipolar | Double | Silicone | Antimicrobial coating | | Platinum-Iridium (Pt/IR) Alloy | Hydrogel electrode |
| | Triple | Silicone with Polytetrafluoro-ethylene (PTFE) | Anti-Inflamatory coating | | Pt/Ir coated with Titanium Nitride | Spiral electrode |
| | Coaxial | | Lubricous coating | | Carbon | Steroid eluting |

Either silicone or polyurethane is a suitable material for the implantable lead-receiver body 59. Both materials have proven to have desirable qualities which are not available in the other. Permanently implantable pacemaker leads made of polyurethane are susceptible to some forms of degradation over time. The identified mechanisms are Environmental Stress Cracking (ESC) and Metal Ion Oxidation (MIO). Silicone on the other hand is a softer material, therefore lead body has to be made bigger. In the presently preferred embodiment silicone re-enforced with polytetrafluroethyene (PTFE) is used.

Nerve-electrode interaction is an integral part of the stimulation system. As a practical benefit of modular design, any type of electrode described below can be used as the distal (cathode) stimulating electrode, without changing fabrication methodology or procedure significantly. When a standard electrode made of platinum or platinum/iridium is placed next to the nerve, and secured in place, it promotes an inflammatory response that leads to a thin fibrotic sheath around the electrode over a period of 1 to 6 weeks. This in turn leads to a stable position of electrode relative to the nerve, and a stable electrode-tissue interface, resulting in reliable stimulation of the nerve chronically without damaging the nerve.

Alternatively, other electrode forms that are non-traumatic to the nerve such as hydrogel, platinum fiber, or steroid elution electrodes may be used with this system. The concept of hydrogel electrode for nerve stimulation is shown schematically in FIG. 26. The hydrogel material 100 is wrapped around the nerve 54, with tiny platinum electrodes 102 being pulled back from nerve. Over a period of time in the body, the hydrogel material 100 will undergo degradation and there will be fibrotic tissue buildup. Because of the softness of the hydrogel material 100, these electrodes are non-traumatic to the nerve.

Figures 26, 27:
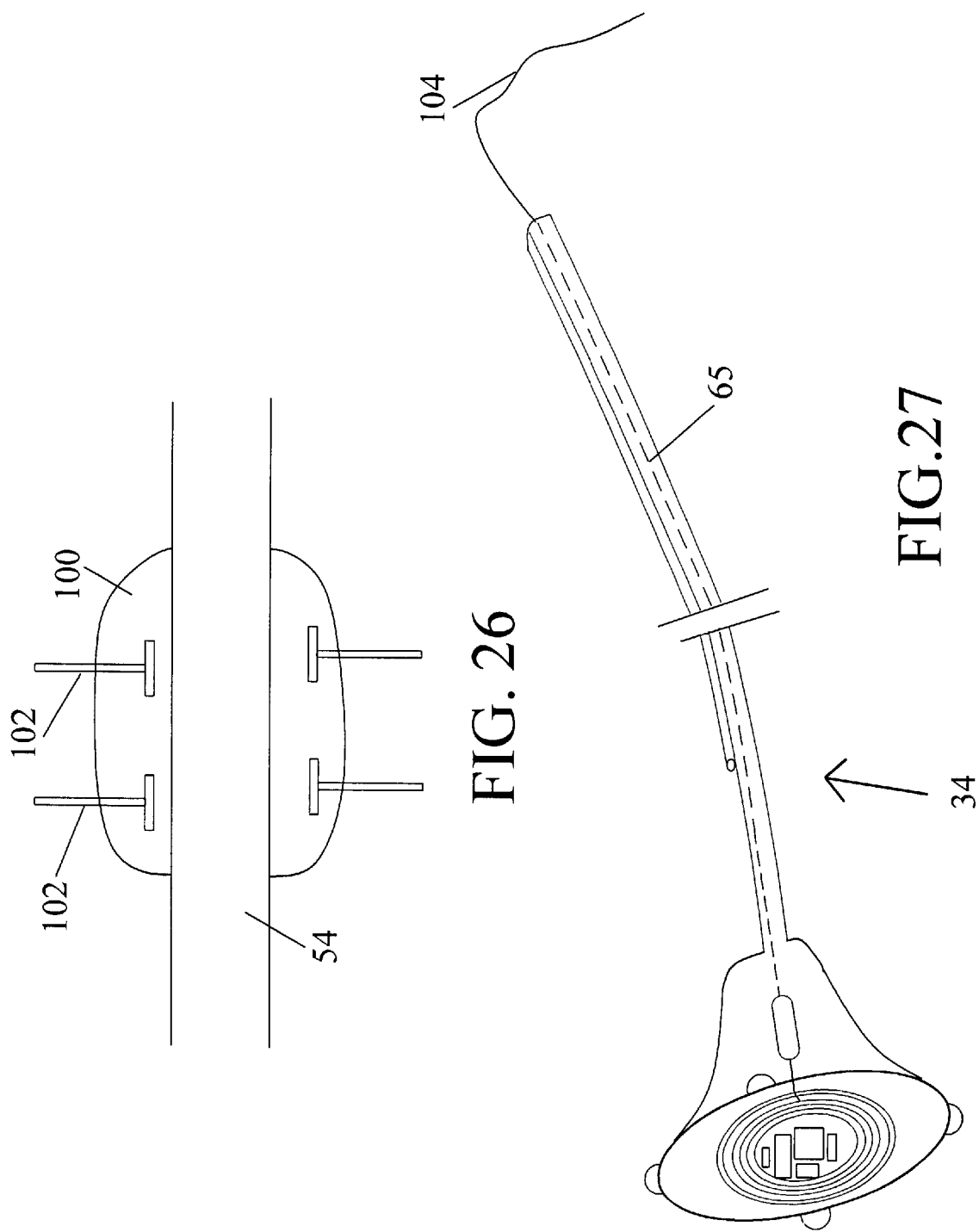
FIG. 26 is a diagram of a hydrogel electrode.
FIG. 27 is a diagram of a lead-receiver utilizing a fiber electrode at the distal end.
Figure 28:
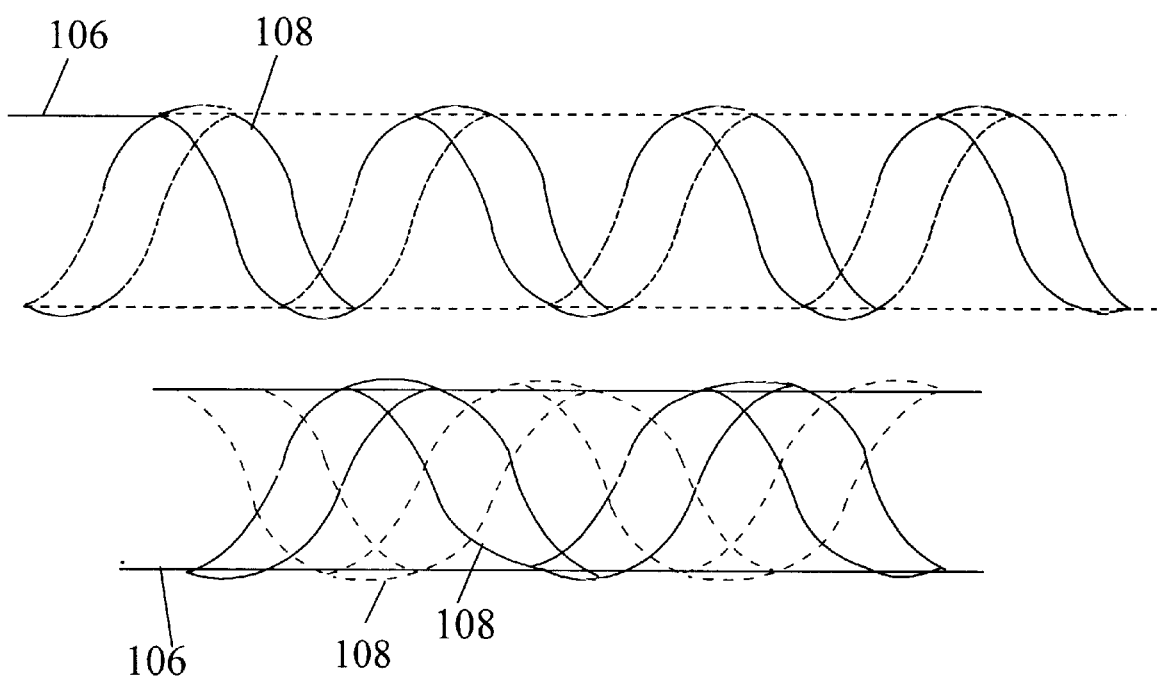
FIG. 28 is a diagram of a fiber electrode wrapped around Dacron polyester.
Figure 29:
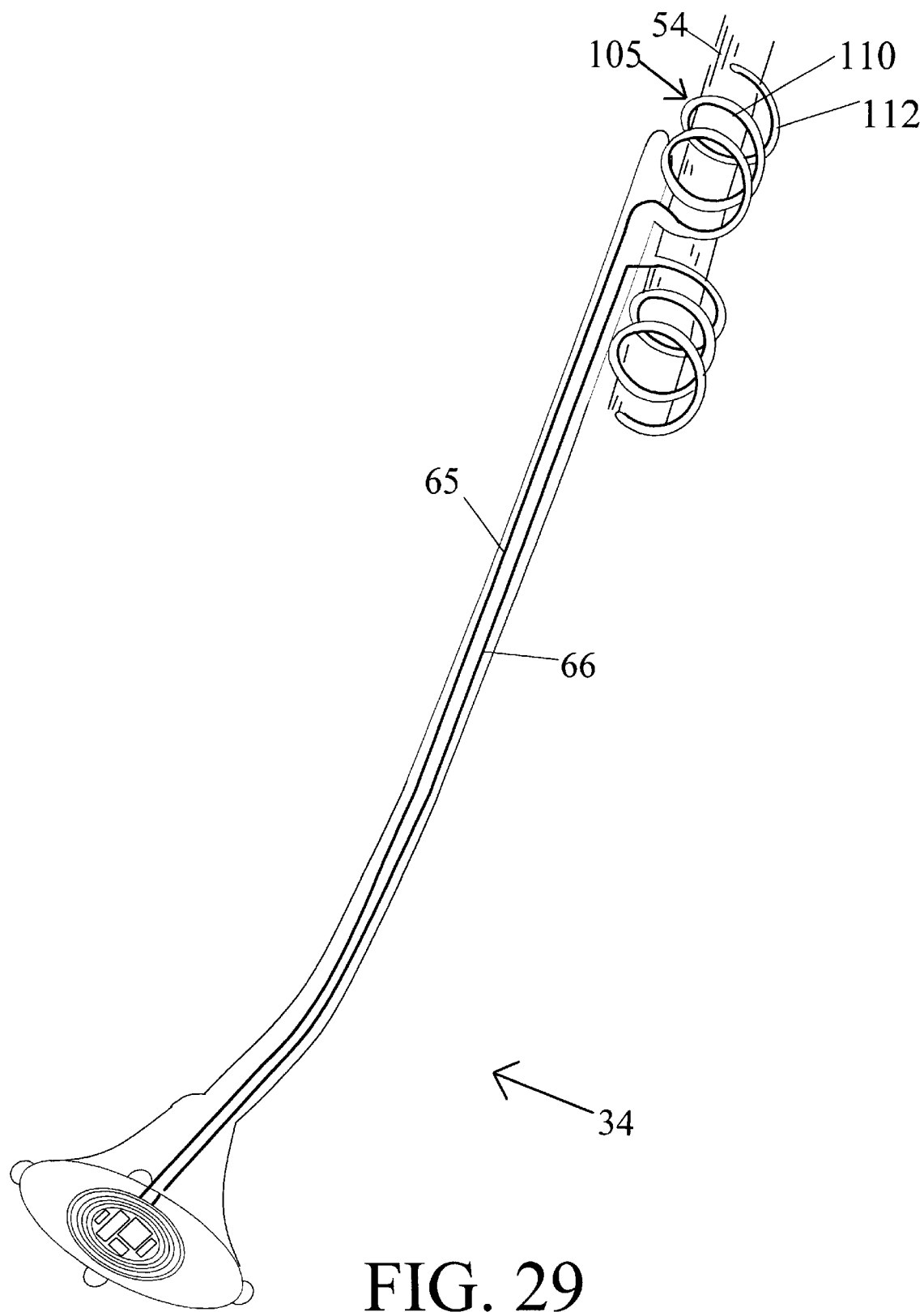
FIG. 29 is a diagram of a lead-receiver with a spiral electrode.

The concept of platinum fiber electrodes is shown schematically in FIG. 27. The distal fiber electrode 104 attached to the lead-receiver 34 may be platinum fiber or cable, or the electrode may be thin platinum fiber wrapped around Dacron polyester or Polyimide 106. As shown in FIG. 28, the platinum fibers 108 may be woven around Dacron polyester fiber 106 or platinum fibers 108 may be braided. At implant, the fiber electrode 104 is loosely wrapped around the surgically isolated nerve, then tied loosely so as not to constrict the nerve or put pressure on the nerve. As a further extension, the fiber electrode may be incorporated into a spiral electrode 105 as is shown schematically in FIG. 29. The two "pigs tail" coil electrodes are made from thin platinum coated braided yarn which is adhered to a substrate in the shape of a "pigs tail" and wraps around the nerve. The braid then continues up a silicone tube lead body.

Figure 30:
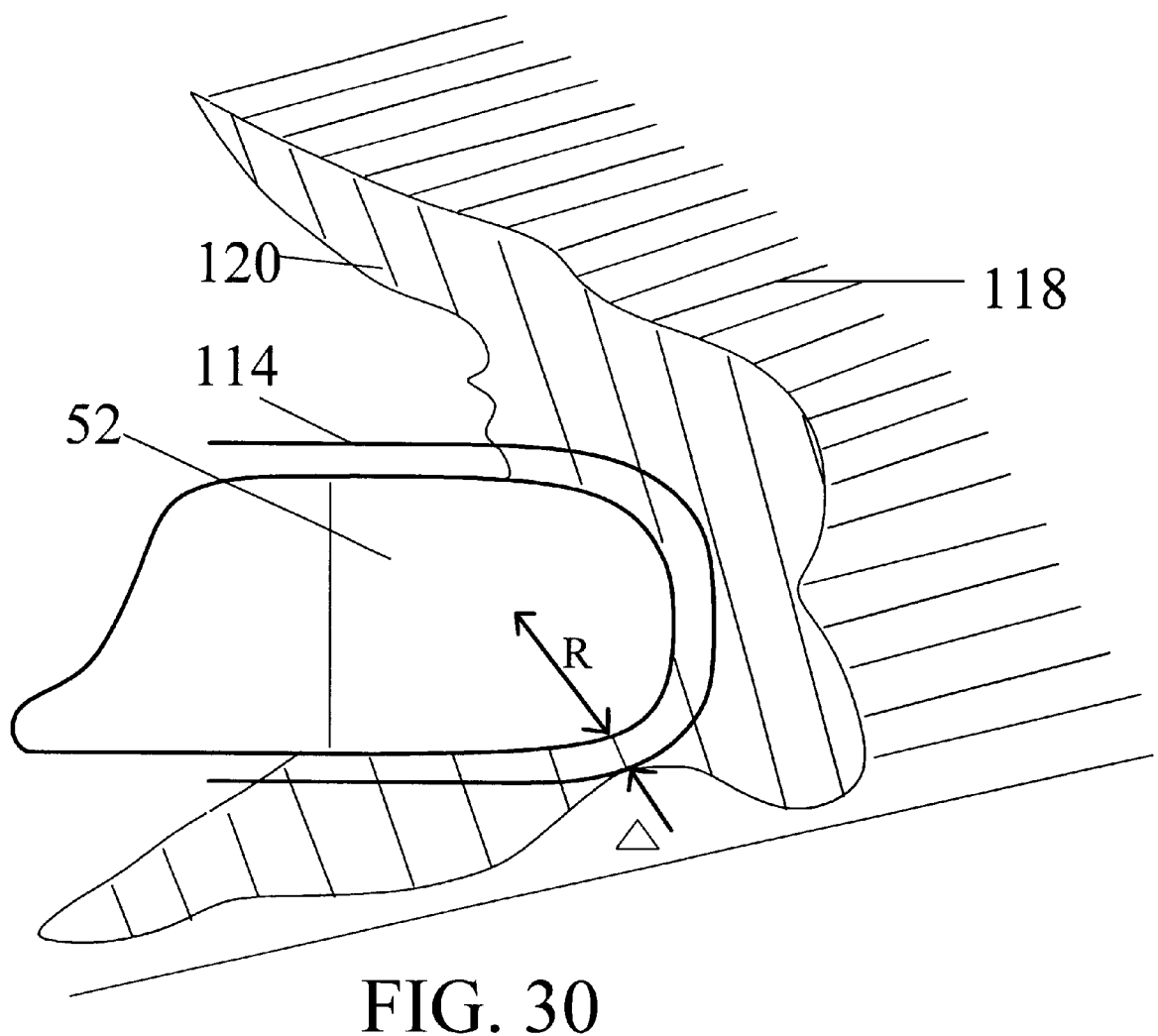
FIG. 30 is a diagram of an electrode embedded in tissue.

Alternatively, steroid elution electrodes may be used. After implantation of a lead in the body, during the first few weeks there is buildup of fibrotic tissue in-growth over the electrode and to some extent around the lead body. This fibrosis is the end result of body's inflammatory response process which begins soon after the device is implanted. The fibrotic tissue sheath has the net effect of increasing the distance between the stimulation electrode (cathode) and the excitable tissue, which is the vagal nerve in this case. This is shown schematically in FIG. 30, where electrode 52 when covered with fibrotic tissue becomes the "virtual" electrode 114. Non-excitable tissue is depicted as 120 and excitable tissue as 118. A small amount of corticosteroid, dexamethasone sodium phosphate, which is commonly referred to as "steroid" or "dexamethasone" placed inside or around the electrode, has significant beneficial effect on the current or energy threshold, i.e. the amount of energy required to stimulate the excitable tissue. This is well known to those familiar in the art, as there is a long history of steroid elution leads in cardiac pacing application. It takes only about 1 mg of dexamethasone to produce the desirable effects. Three separate ways of delivering the steroid drug to the electrode nerve-tissue interface are being disclosed here. Dexamethasone can be placed inside an electrode with microholes, it can be placed adjacent to the electrode in a silicone collar, or it can be coated on the electrode itself.

Figure 31:
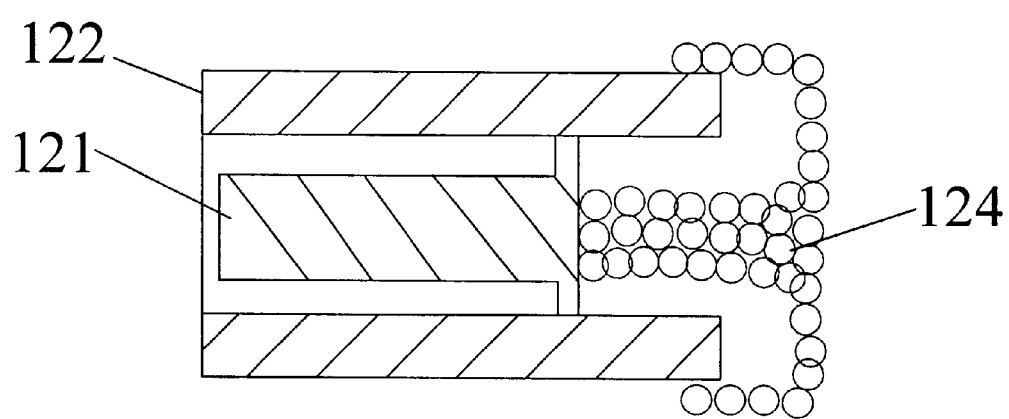
FIG. 31 is a diagram of an electrode containing steroid drug inside.

Dexamethasone inside the stimulating electrode is shown schematically in FIG. 31. A silicone core that is impregnated with a small quantity of dexamethasone 121, is incorporated inside the electrode. The electrode tip is depicted as 124 and electrode body as 122. Once the lead is implanted in the body, the steroid 121 elutes out through the small holes in the electrode. The steroid drug then has anti-inflammatory action at the electrode tissue interface, which leads to a much thinner fibrotic tissue capsule.

Another way of having a steroid eluting nerve stimulating electrode, is to have the steroid agent placed outside the distal electrode 91 in a silicone collar 126. This is shown schematically in FIG. 32. Approximately 1 mg of dexamethasone is contained in a silicone collar 126, at the base of the distal electrode 52. With such a method, the steroid drug elutes around the electrode 52 in a similar fashion and with similar pharmacokinetic properties, as with the steroid drug being inside the electrode.

Another method of steroid elution for nerve stimulation electrodes is by coating of steroid on the outside (exposed) surface area of the electrode. This is shown schematically in FIG. 33. Nafion is used as the coating matrix. Steroid membrane coating on the outside of the electrode is depicted as 128. The advantages of this method are that it can easily be applied to any electrode, fast and easy manufacturing, and it is cost effective. With this method, the rate of steroid delivery can be controlled by the level of sulfonation.

A schematic representation of the cross section of different possible lumens is shown in FIG. 34. The lead body 59 can have one, two, or three lumens for conducting cable, with or without a hollow lumen. In the cross sections, 132A–F represents lumens(s) for conducting cable, and 134A–C represents hollow lumen for an aid in implanting the lead.

Additionally, different classes of coating may be applied to the implantable lead-receiver 34 after fabrication. These coatings fall into three categories, lubricious coating, antimicrobial coating, and anti-inflammatory coating.

The advantage of modular fabrication is that with one technology platform, several derivative products or models can be manufactured. As a specific practical example, using a silicone lead body platform, three separate derivative or lead models can be manufactured by using three different electrodes such as standard ball electrode, spiral electrode, or steroid electrode. This is made possible by designing the fabrication steps such that the distal electrodes are assembled at the end, and as long as the electrodes are mated to the insulation and conducting cable, the shape or type of electrode does not matter. Similarly, different models can be produced by taking a finished lead and then coating it with lubricious coating or antimicrobial coating. In fact, considering the design variables disclosed in Table 1, a large number of combinations are possible.

While various embodiments of the present invention have been described in detail, it is apparent that modifications and adaptations of those embodiments will occur to those skilled in the art. However, it is to be expressly understood that such modifications and adaptations are within the spirit and scope of the present invention.

What is claimed is:

1. An apparatus for adjunct (add-on) therapy for obesity and compulsive eating disorders by neuromodulating a vagus nerve of a patient, comprising;
    a) an implantable lead-receiver comprising, circuitry, a secondary coil, and at least one electrode adapted to be in contact with said vagus nerve;
    b) an ambulatory external stimulator for delivering therapy for obesity and compulsive eating disorders; said external stimulator comprising a power source, circuitry to emit electrical signals, a computer readable medium encoded with at least two pre-determined programs of said electrical signals, and a primary coil;
    c) a regulation means to adjust said electrical signals delivered from said stimulator to said lead-receiver;
    d) said primary coil and said secondary coil being capable of forming an electrical connection by inductive coupling,
    whereby said apparatus delivers therapy for obesity and compulsive eating disorders.

2. The apparatus of claim 1, wherein said external stimulator further comprises a means for patient override mechanism to manually activate said external stimulator.

3. The apparatus of claim 1, wherein said apparatus further comprises means to modify said at least two predetermined programs controlling said electrical signals.

4. The apparatus of claim 1, wherein said apparatus further comprising a means for selective operation of one of said at least two predetermined programs.

5. The apparatus of claim 1, wherein said apparatus further comprises a means to sense proximity between said primary and said secondary coils.

6. The apparatus of claim 1, wherein said external stimulator has wireless communication means, to remotely control from a distance, said at least two predetermined programs.

7. The apparatus of claim 6, wherein the remote control is via the wireless internet medium.

8. The apparatus of claim 7, wherein the wireless internet remote control utilizes wireless access protocol (WAP).

9. The apparatus of claim 1, wherein said lead-receiver further comprises a lead body with at least one lumen, a lead body insulation, a conductor.

10. The apparatus of claim 9, wherein said at least one lumen is selected from the group consisting of single, double, triple and coaxial lumens.

11. The apparatus of claim 9 wherein said lead body insulation is selected from the group consisting of polyurethane, silicone, and silicone with polytetrafluoroethylene (PTFE).

12. The apparatus of claim 9 wherein said lead body further comprises a coating selected from the group consisting of lubricious PVP, antimicrobial and anti-inflammatory coatings.

13. The apparatus of claim 9 wherein said electrode comprises a material selected from the group consisting of platinum, platinum/iridium alloy, platinum/iridium alloy coated with titanium nitride and carbon.

14. The apparatus of claim 9 wherein said electrode is selected from the group consisting of, spiral electrodes, hydrogel electrodes, steroid eluting electrodes, and standard ball electrodes.

15. The apparatus of claim 1, wherein said electrical signals comprise at least one variable component selected from the group consisting of the current amplitude, pulse width, frequency and on-off timing sequence, and said at least two predetermined programs controls said variable component of said electrical signals.

16. The apparatus of claim 1, wherein said vagus nerve is stimulated by means for bipolar stimulation.

17. The apparatus of claim 1, wherein said cranial nerve is stimulated by means for unipolar stimulation.

18. The apparatus of claim 1, wherein, said external stimulator further compromises means to lockout at least one of said at least two predetermined programs to the patient.

19. A system for adjunct (add-on) therapy for obesity and compulsive eating disorders by neuromodulating a vagus nerve of a patient, that can be remotely controlled using the internet, comprising,
    a) an implantable lead-receiver comprising circuitry, a secondary coil, and at least one electrode adapted to be in contact with said vagus nerve;
    b) an ambulatory external stimulator for delivering therapy for obesity and compulsive eating disorders wherein said external stimulator comprising a power source, circuitry to emit electrical signals, a computer readable medium encoded with at least two predetermined programs of said electrical signals, and a primary coil;

c) a regulation means to regulate said electric signals delivered from said external stimulator to said implantable lead-receiver;

d) said primary coil and said secondary coil being capable of forming an electrical connection by inductive coupling;

e) a telemetry means for remotely controlling said predetermined programs over the internet, whereby said system delivers neuromodulation therapy for obesity and compulsive eating disorders which can be remotely controlled over the internet.

20. The system of claim 19, wherein said external stimulator further comprises a means for patient override mechanism to manually activate said external stimulator means.

21. The system of claim 19, wherein said system further comprises means to modify said at least two predetermined programs controlling said electrical signals.

22. The system of claim 19, wherein said system further comprising a means of selective operation of one of said at least two predetermined programs.

23. The system of claim 19, wherein said system further comprises a means for proximity sensing between said primary and said secondary coils.

24. The system of claim 19, wherein said neuromodulation of vagus nerve comprises bilateral neuromodulation of vagus nerve.

25. The system of claim 19, wherein said bilateral neuromodulation of vagus nerve comprises subdiaphramatic level neuromodulation.

26. The system of claim 24, wherein said bilateral neuromodulation of vagus nerve further comprises neck level neuromodulation.

27. The system of claim 19, wherein said wireless internet remote control utilizes wireless access protocol (WAP).

28. The system of claim 19, wherein said lead-receiver further comprises a lead body with at least one lumen, a lead body insulation, a conductor.

29. The system of claim 28, wherein said at least one lumen is selected from the group consisting of single, double, triple and coaxial lumens.

30. The system of claim 28 wherein said lead body insulation is selected from the group consisting of polyurethane, silicone, and silicone with polytetrafluoroethylene (PTFE).

31. The system of claim 28 wherein said lead body further comprises a coating selected from the group consisting of lubricious PVP, antimicrobial and anti-inflammatory coatings.

32. The system of claim 28 wherein said electrode comprises a material selected from the group consisting of platinum, platinum/iridium alloy, platinum/iridium alloy coated with titanium nitride and carbon.

33. The system of claim 28 wherein said electrode is selected from the group consisting of, spiral electrodes, hydrogel electrodes, steroid eluting electrodes, and standard ball electrodes.

34. The system of claim 19, wherein said electrical signals comprise at least one variable component selected from the group consisting of the current amplitude, pulse width, frequency and on-off timing sequence, and said at least two predetermined programs controls said variable component of said electrical signals.

35. The system of claim 19, wherein said vagus nerve is neuromodulated by means for bipolar stimulation.

36. The system of claim 19, wherein said cranial nerve is neuromodulated by means for unipolar stimulation.

37. The system of claim 19, wherein, said external stimulator further compromises means to lockout at least one of said at least two predetermined programs to the patient.

38. A method for neuromodulating a vagus nerve for treatment of obesity and compulsive eating disorders, comprising;

a) selecting a predetermined program to control the output of an external stimulator;

b) activating said external stimulator to emit electrical signals in accordance with said predetermined program; and c) inductively coupling said external stimulator with an implantable lead-receiver to stimulate a vagus nerve, d) regulating said electric signals delivered from said external stimulator to said implantable lead-receiver by regulation means, whereby neuromodulation therapy is provided to said vagus nerve for treatment of obesity and compulsive eating disorders.

39. The method of claim 38, further comprising implanting beneath the skin of a patient said lead-receiver adapted to be in electrical contact with said vagus nerve.

40. A method of treating obesity and compulsive eating disorders by providing pulsed electrical stimulation to a vagus nerve of a patient, comprising the steps of:

a) providing an implantable lead-receiver comprising, circuitry, a secondary coil, and at least one electrode adapted to be in contact with said vagus nerve;

b) providing an external stimulator for providing therapy for obesity and compulsive eating disorders; said stimulator comprising circuitry to emit electrical signals, at least two predetermined programs to control said electrical signals, a primary coil and a power supply;

c) activating one of said at least two programs of said external stimulator;

d) inductively transferring said electrical signals from said primary coil to said secondary coil;

whereby said electrical signals stimulate the vagus nerve according to at least one of said at least two predetermined programs to provide therapy for obesity and compulsive eating disorders.

41. The method of claim 40, wherein said vagus nerve is a left vagus nerve.

42. The method of claim 40, wherein said external stimulator further comprises means to modify said predetermined programs controlling said electrical signals.

43. The method of claim 40, wherein a proximity sensing means is used for optimally positioning the primary coil relative to said secondary coil.

44. The method of claim 40, wherein said external stimulator has wireless communication means to remotely control said at least two predetermined programs.

45. The method of claim 40, wherein said vagus nerve is stimulated by means for bipolar stimulation.

46. The method of claim 40, wherein said cranial nerve is stimulated by means for unipolar stimulation.

47. The method of claim 40, further comprising means for manually controlling said electrical signals to stimulate said vagus nerve.

48. The method of claim 40, wherein a) said electrical signals comprise at least one variable component selected from the group consisting of the current amplitude, pulse width, frequency, and on-off timing sequence; and b) said at least two predetermined programs controls said variable component of said electrical signals.

49. The method of claim 40, further comprising a means to manually disengage said at least two predetermined programs.

50. The method of claim 40, wherein, said stimulator further compromises means to lock out at least one of said at least two predetermined programs to the patent.

51. A method of providing adjunct (add-on) therapy for obesity and compulsive eating disorders by electrical stimulation of a vagus nerve of a patient, comprising the steps of:

a) providing an implantable lead-receiver comprising, circuitry, a secondary coil, and at least one electrode adapted to be in contact with said vagus nerve;

b) providing an external stimulator comprising, circuitry to emit electrical signals, at least two predetermined programs of electrical signals to provide therapy for obesity and compulsive eating disorders, an external coil and a power supply;

c) activating one of said at least two predetermined programs of said external stimulator;

d) inductively transferring said electrical signals from said primary coil to said secondary coil;

e) providing regulating means to adjust electric signals transferred from said primary coil to said secondary coil of said implantable lead-receiver;

whereby, said electrical signals stimulate said vagus nerve according to at least one of said at least two predetermined programs for providing therapy for obesity and compulsive eating disorders.

52. The method of claim 51, wherein stimulation to said vagus nerve comprises bilateral vagus stimulation.

53. The method of claim 51, wherein said vagus nerve stimulation comprises subdiaphramatic level stimulation.

54. The method of claim 51, wherein said vagus nerve stimulation comprises stimulation at the neck level.

55. The method of claim 51, wherein said external stimulator further comprises means to modify said at least two predetermined programs controlling said electrical signals.

56. The method of claim 51, wherein a proximity sensing means is used for optimally positioning said primary coil relative to said secondary coil.

57. The method of claim 51, wherein said external stimulator has wireless communication means to remotely control said at least two predetermined programs.

58. The method of claim 57, wherein, said wireless communication means utilizes Wireless Access Protocol (WAP).

59. The method of claim 51, wherein said vagus nerve is stimulated by means for bipolar stimulation.

60. The method of claim 51, wherein said cranial nerve is stimulated by means for unipolar stimulation.

61. The method of claim 51, further comprising means to activate one of said at least two predetermined programs manually.

62. The method of claim 51, wherein a) said electrical signals comprise at least one variable component selected from the group consisting of the current amplitude, pulse width, frequency, and on-off timing sequence; and b) said at least two predetermined programs controls said variable component of said electrical signals.

63. The method of claim 51, wherein, said stimulator further compromises means to lock out at least one of said at least two predetermined programs to the patient.

* * * * *